(12) United States Patent
Mullen et al.

(10) Patent No.: US 9,884,838 B2
(45) Date of Patent: Feb. 6, 2018

(54) STABILIZED LEVULINIC ESTER KETALS

(71) Applicant: GFBiochemicals Limited, Valletta (MT)

(72) Inventors: Brian D. Mullen, Delano, MN (US); Vivek Badarinarayana, St. Louis Park, MN (US); Eric S. Hall, Plymouth, MN (US); Matthew J. Tjosaas, Minneapolis, MN (US); Cora M. Leibig, Maple Grove, MN (US)

(73) Assignee: GFBIOCHEMICALS LIMITED, Valletta (MT)

( * ) Notice: Subject to any disclaimer, the term of this patent is extended or adjusted under 35 U.S.C. 154(b) by 57 days.

(21) Appl. No.: 15/223,925

(22) Filed: Jul. 29, 2016

(65) Prior Publication Data
US 2016/0332983 A1    Nov. 17, 2016

Related U.S. Application Data

(62) Division of application No. 13/648,252, filed on Oct. 9, 2012, now abandoned.

(60) Provisional application No. 61/545,849, filed on Oct. 11, 2011.

(51) Int. Cl.
*C07D 317/30* (2006.01)
*C09D 7/12* (2006.01)

(52) U.S. Cl.
CPC .......... *C07D 317/30* (2013.01); *C09D 7/125* (2013.01)

(58) Field of Classification Search
CPC .............................. C07D 317/30; C09D 7/125
See application file for complete search history.

(56) References Cited

U.S. PATENT DOCUMENTS

| 4,737,426 A | 4/1988 | Roth |
| 5,998,092 A | 12/1999 | McCulloch et al. |
| 6,610,765 B1 | 8/2003 | Pfaendner |
| 7,815,950 B2 | 10/2010 | Kobler et al. |
| 2007/0021566 A1 | 1/2007 | Tse et al. |
| 2008/0242721 A1 | 10/2008 | Selifonov |
| 2009/0186966 A1 | 7/2009 | Gallucci et al. |
| 2012/0122745 A1 | 5/2012 | Mullen et al. |

FOREIGN PATENT DOCUMENTS

| WO | WO 2009/032905 | 3/2009 |
| WO | WO 2009/048874 | 4/2009 |
| WO | WO 2009/049041 | 4/2009 |
| WO | WO 2010/036884 | 4/2010 |
| WO | WO 2010/151558 | 12/2010 |
| WO | WO 2011/032095 | 3/2011 |

OTHER PUBLICATIONS

Gelas, Carbohydrate Research 30(1), 21-34 (1973).
Carey, F.A. and Sundberg, R.J. "Advanced Organic Chemistry Part B: Reactions and Synthesis" $2^{nd}$ ed. 1983, Plenum Press, NY p. 544.
Ono et al., J. Am. Oil Chem. Soc. 70(1), 29 (1993).
International Search Report and Written Opinion from related PCT Application PCT/US2012/059537, dated Mar. 29, 2013, 6 pages.
Leibig, et al., "Cellulosic-derived levulinic ketal esters: a new building block", Renewable and Sustainable Polymers, American Chemical Society, Chapter 7, pp. 111-116, Apr. 21, 2011.
International Preliminary Report on Patentability from related PCT Application PCT/US2012/059537, dated Apr. 15, 2014, 10 pages.
Kovarik, P., "Kinetic Study of Action of Additives in Poly (Vinyl Chloride) Stabilizer Systems I. Sterically Hindered Phenolic Antioxidants." Chemical Papers 51.5 (1997): 245-251.
Cortolano, F.P., "Antioxidants and UV stabilizers: A summary of their utilization in PVC." Journal of Vinyl Technology 15.2 (1993): 69-75.

*Primary Examiner* — Matt Mauro
(74) *Attorney, Agent, or Firm* — Norton Rose Fulbright US LLP

(57) ABSTRACT

The invention describes methods of preparation and compositions of plasticizers. The plasticizers include at least 2 alkyl ketal ester moieties and have a molecular weight of greater than 300. In one aspect, the alkyl ketal ester moieties are levulinic ester ketals. Certain compositions contain at least one of an antioxidant, a UV stabilizer, a thermal stabilizer or mixtures thereof, present in the composition from about 0.01 to about 5.0 percent by weight of the total composition.

4 Claims, No Drawings

STABILIZED LEVULINIC ESTER KETALS

CROSS REFERENCE TO RELATED APPLICATIONS

This application is a Divisional of U.S. application Ser. No. 13/648,252, filed Oct. 9, 2012, which claims the benefit under 35 U.S.C. 119(e) to U.S. Provisional Patent Application No. 61/545,849, filed Oct. 11, 2011. The disclosures of which are incorporated by reference herein.

FIELD OF THE INVENTION

The invention relates generally to the preparation of stabilized alkyl ketal ester plasticizers having at least 2 alkyl ketal ester moieties, such as those derived from levulinic acid, with a molecular weight of greater than 300 and compositions thereof.

BACKGROUND OF THE INVENTION

Many known chemical products such as surfactants, plasticizers, solvents, and polymers are currently manufactured from non-renewable, expensive, petroleum-derived or natural gas-derived feedstock compounds. High raw material costs and uncertainty of future supplies requires the discovery and development of surfactants, plasticizers, solvents, and polymers that can be made from inexpensive renewable biomass-derived feedstocks and by simple chemical methods. Using renewable resources as feedstocks for chemical processes will reduce the demand on non-renewable fossil fuels currently used in the chemical industry and reduce the overall production of carbon dioxide, the most notable greenhouse gas.

A potential source of materials that are useful as chemical building blocks are cyclic ketals and acetals of oxocarboxylates with polyols. Polyhydric alcohols, or polyols, having 1,2 and 1,3 hydroxy conformations can react with a ketone or aldehyde to form a cyclic ketal or an acetal (Carey, F. A. and Sundberg, R. J., "Advanced Organic Chemistry Part B: Reactions and Synthesis" 2nd ed., 1983, Plenum Press, NY, N.Y., p. 544).

Diols such as 1,2-ethane diol (ethylene glycol) and 1,3 propanediol (propylene glycol) are examples of such polyols. Diols having a 1,2 hydroxyl group configuration form dioxolanes when reacted with ketone or aldehyde moieties, while 1,3 diols form dioxanes.

The use of levulinate compounds and glycerol based compounds is particularly useful as both of these starting materials arise from renewable feedstocks. Further, the ketal reaction products are useful for synthesis of a wide variety of surfactants, plasticizers, polymers, and the like. Other reaction products of oxocarboxylates (such as pyruvic acid, acetoacetic acid, or esters thereof, and the like) with triols (such as trimethylolpropane, trimethylolethane, and the like) are disclosed in International Patent Application No. PCT/US08/75225. The methods employed to synthesize these compounds involve the formation of one mole of water with each mole of ketal formed. Likewise, polyketal compounds are formed from oxocarboxylates and tetrols and higher polyols using similar methods, with one mole of water formed for each mole of ketal functionality formed. Polyketal compounds are described in International Patent Application No. PCT/US08/079337. One example of a polyketal is a bisketal formed from a levulinate ester and erythritol (or a stereoisomer thereof):

Synthetic routes to form ketals of oxocarboxylic acids or the esters thereof are described in International Patent Application No. PCT/US08/079083. The methodology disclosed therein employs very low levels of acid catalyst and certain stoichiometric ratios of oxocarboxylate to polyol to result in high yields of ketal compounds with short reaction times. However, this methodology, as well as previous methods used to form ketals from oxocarboxylates and polyols, necessarily involves the formation of water in conjunction with formation of the ketal end product. Because ketal formation is reversible in the presence of water and the acid catalyst, rigorous removal of water is necessary in order to drive the reaction and maintain high yields and product stability. Additionally, the main side products in the reaction of tetrols and higher polyols to form polyketals are typically those where less than the full desired complement of oxocarboxylate is reacted—e.g., a tetrol such as erythritol or diglycerol having one ketal functionality instead of two; or a hexitol such as mannitol having one or two ketal functionalities instead of three. Such side products are difficult to separate from the desired end product, necessitating fractionation. Further, the free hydroxyl groups present in these side products can undergo side reactions in subsequent polymerization reactions or create incompatibility with one or more formulation components in the application of bisketal and trisketal compounds as plasticizers, solvents, and the like.

Additionally, the structural variation of the ketal and polyketal compounds disclosed in the above cited patent applications and publications are limited to the variation in the polyol and oxocarboxylate compounds employed.

It is desirable to provide new starting materials and synthetic routes to form new varieties of chemical building blocks for monomers, plasticizers, surfactants, and polymers. It is desirable to provide chemical building blocks that arise solely from renewable feedstocks. It is desirable to facilitate synthesis of chemical building blocks that is simple, inexpensive, and scalable for commercialization purposes. It is desirable to avoid the problem of water formation in the ketalization of oxocarboxylic acids or their esters. It is also desirable to obtain such starting materials that are stable and/or have high purity.

Therefore, a need exists that overcomes one or more of the current disadvantages noted above.

BRIEF SUMMARY OF THE INVENTION

It is desirable to provide commonly used materials, such as surfactants, plasticizers, solvents, and polymers, from renewable feedstocks as a source of chemical building blocks. It is also desirable to provide chemical building blocks that are chemically and thermally stable. Furthermore, chemical building blocks having multiple functionalities for subsequent reactions are often desirable. The ability to provide such materials by simple and reproducible methods that can be carried out with ease is advantageous.

The present invention surprisingly provides compositions of alkyl ketal ester plasticizers having at least 2 alkyl ketal ester moieties with a molecular weight of greater than 300 and at least one of an antioxidant, a UV stabilizer, a thermal stabilizer or mixtures thereof, present in the composition from about 0.01 to about 5.0 percent by weight of the total composition. Prior to the invention, alkyl ketal ester plasticizers were not stable and would degrade with time and/or contained impurities that would cause the plasticizer to decompose.

In one aspect, the alkyl ester moieties are levulinic ester ketals.

In another aspect, methods are provided to prepare the 2 alkyl ketal ester moieties with a molecular weight of greater than 300. The methods provide stabilized products unavailable until the present invention.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

DETAILED DESCRIPTION

In the specification and in the claims, the terms "including" and "comprising" are open-ended terms and should be interpreted to mean "including, but not limited to. . . ." These terms encompass the more restrictive terms "consisting essentially of" and "consisting of."

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

In one aspect, a composition is provided that includes a plasticizer, as described herein, having at least 2 alkyl ketal ester moieties with a molecular weight of greater than 300 and at least one of an antioxidant, a UV stabilizer, a thermal stabilizer or mixtures thereof, present in the composition from about 0.01 to about 5.0 percent by weight of the total composition.

In another aspect, a plasticizer is provided comprising at least 2 alkyl ketal ester moieties. The plasticizer has a molecular weight of greater than 300 comprising a formula of:

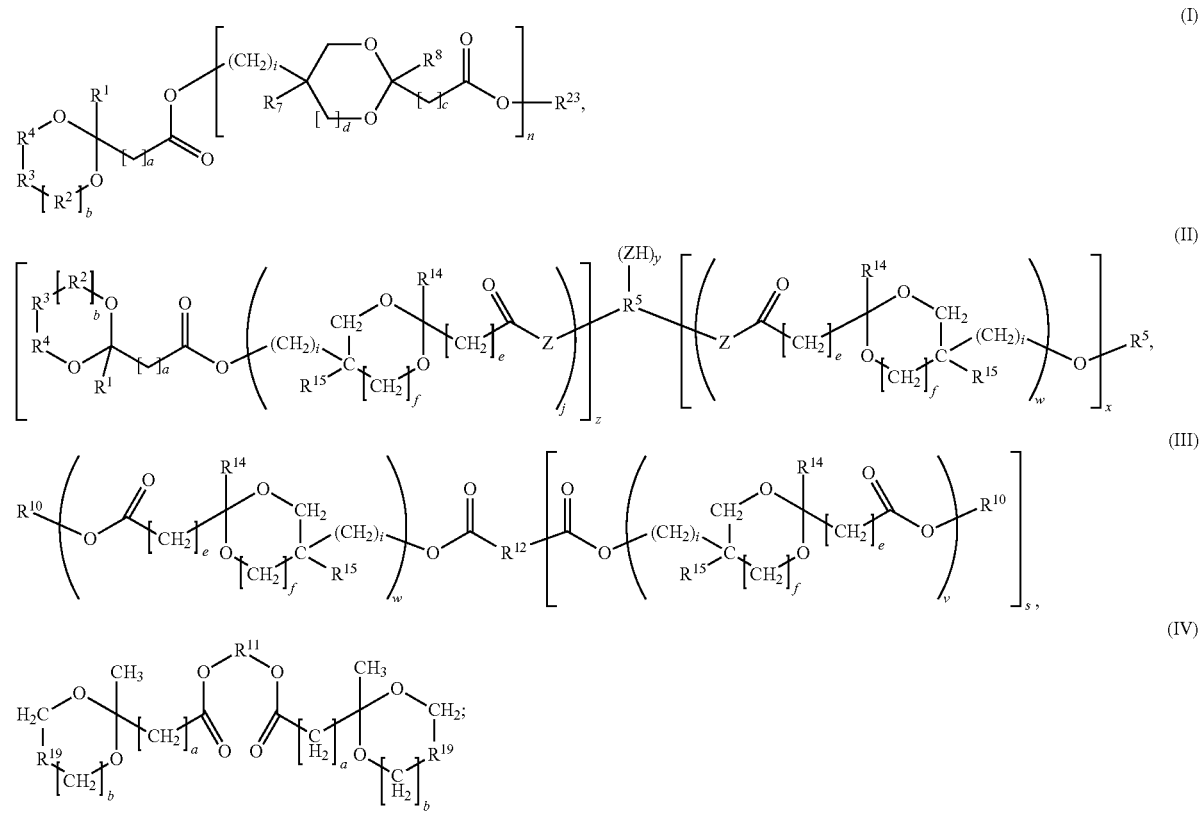

or combinations thereof, wherein
each a, independently, is from 0 or an integer of 1 to 12;
each b, independently, is 0 or 1;
c is from 0 to 12;

d is 0 or 1;
each e, independently, is from 0 to 12;
each f, independently, is from 0 to 12;
each i is 0 or 1;
each j, independently, is 0 to 100;
each $R^1$, independently, is a hydrogen, a hydrocarbyl group, or a substituted hydrocarbyl group;
each $R^2$, $R^3$ and $R^4$ are independently methylene, alkylmethylene, or dialkylmethylene;

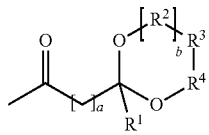

$R^5$ is a hydrogen or
$R^6$ is a hydrocarbyl group or a substituted hydrocarbyl group;
each $R^7$, independently, is a hydrogen, a hydrocarbyl or a substituted hydrocarbyl group;
each $R^8$, independently, is a hydrogen, a hydrocarbyl or a substituted hydrocarbyl group;
each $R^{10}$, independently, is a hydrocarbyl or a substituted hydrocarbyl group;
$R^{11}$ is a hydrocarbyl, a substituted hydrocarbyl, or a hydrocarbyl group terminated with one or more heteroatoms to form a cyclic membered ring and which can include one or more of —O—, —NH—, —NR—, wherein R is a hydrocarbyl or a substituted hydrocarbyl;
$R^{12}$, is a covalent bond, a hydrocarbyl group or a substituted hydrocarbyl group;
each $R^{14}$, independently, is a hydrogen, a hydrocarbyl, or a substituted hydrocarbyl group;
each $R^{15}$, independently, is a hydrogen, a hydrocarbyl, or a substituted hydrocarbyl group;
each $R^{19}$, independently, is a hydrocarbyl, a substituted hydrocarbyl, or a hydrocarbyl group substituted with up to 5 hydroxyl groups;
each $R^{23}$ is a hydrocarbyl group or substituted hydrocarbyl group having between 1 and 12 carbon atoms
each Z, independently, is —O—, —NH— or —NR— where R is a hydrocarbyl or a substituted hydrocarbyl group;
n is from 1 to 100;
s is at least one;
v is from 0 to 100;
w is from 1 to 100;
x is at least 1;
y is 0 or a positive number; and
z is 0 or a positive number provided that z is at least one when $R^5$ is hydrogen. In one aspect, the plasticizer having at least 2 alkyl ketal ester moieties with a molecular weight of greater than 300 has a color index (YI) of less than 50 measured by ASTM method E313 and has a purity of at least 90%.

In another aspect, the plasticizer having at least 2 alkyl ketal ester moieties with a molecular weight of greater than 300 has a mass loss that is less than 2% after 10 days at 110° C. and less than 15% RH.

In still another aspect, the preparation of the plasticizer is conducted in a manner such that less than about 1000 ppm of oxygen are present in the reaction vessel, more particularly less than about 500 ppm, even more particularly less than about 100 ppm and most particularly, less than about 50 ppm or less.

In one embodiment, the plasticizer is the compound of formula (I) wherein b is 0, i is 1, $R^1$ is a hydrocarbyl, $R^3$ is an alkylmethylene, $R^4$ is a methylene, $R^7$ is a H, $R^8$ is a hydrocarbyl group, $R^{23}$ is a hydrocarbyl group, c is 2, d is 0 and n=1. More specifically, b is 0, i is 1, $R^1$ is a methyl group, $R^3$ is $CH_3CH$, $R^4$ is a methylene, $R^7$ is a H, $R^8$ is a methyl group, $R^{23}$ is an ethyl group, c is 2, d is 0 and n=1.

In another embodiment, the plasticizer is the compound of formula (IV) wherein $R^{11}$ is a C4 alkyl. More specifically, each a=2 and each b=0.

In certain embodiments, $R^{11}$ provides that no two hydroxyl groups should be bonded to the same carbon atom. Suitable polyols include alkane diols such as ethane diol, 1,2-propane diol, 1,3-propane diol, 1,4-butane diol, 1,5-pentane diol and 1,6-hexane diol, 1,4-cyclohexanediol, glycerine, trimethylolpropane, trimethylolethane, pentaerythritol, erythritol, sucrose, isosorbide, sorbitol, bisphenol-A, 2,3-dibromobutene-1,4-diol, 1,4-benzene dimethanol, 1,4-benzenediol (hydroquinone), 2-butyne-1,4-diol, 3-hexyne, 3-5-diol and other alkyne-containing polyols such as those marked under the Surfynol™ brand name by Air Products and Chemicals. Other suitable polyols contain ether groups; these include glycol ethers such as diethylene glycol, triethylene glycol, dipropylene glycol, tripropylene glycol. Other suitable ether-containing polyols include hydroxyl-terminated polyethers such as poly(ethylene oxide), poly(propylene oxide), ethylene oxide-propylene oxide copolymers and polymers of tetramethylene glycol; these may have molecular weights of up to 6000, preferably up to 1000 and more preferably up to 150. The polyol may contain ester linkages; these polyols include those formed by condensation or step-growth polymerization of diols and dicarboxylic acids (or their derivatives), including a polyester of diethylene glycol and phthalic acid or phthalic anhydride.

When Z is —NR— or —NH—, $R^6$ corresponds to the residue, after removal of amino groups, of a polyamine having the formula $R^6(NRH)$ or $R^6(NH_2)$. No two amino groups should be bonded to the same carbon atom. Examples of suitable polyamines include hydrazine, ethane-1,2-diamine, 1,6-hexanediamine, but-2-ene-1,4-diamine, Metformin, butane-1,4-diamine, propane-1,2-diamine, piperazine, 2,2,4-trimethyl-1,6-hexanediamine, 2,4,4-trimethyl-1,6-hexanediamine, benzene-1,3-diamine, 2-methylbenzene-1,3-diamine, 4-chlorobenzene-1,3-diamine, and polyoxyalkyleneamines having two amine groups, such as those sold under the trade name JEFFAMINE®, (Huntsman Corp.; Salt Lake City, Utah), diamines such as those sold under the trade name ELASTAMINE® (Huntsman Corporation), phenylene diamine, methylene bis(aniline), diethyltoluenediamine and the like.

The values of j, w, x, y and z in formula II will depend on factors including the number of hydroxyl or amino groups on the polyol, aminoalcohol or polyamine, the number of moles of alkyl ketal ester per mole of the polyol, aminoalcohol or polyamine, the number of moles of the hydroxyalkyl ketal ester per mole of the polyol, aminoalcohol or polyamine, and the extent to which the reaction is taken towards completion. Higher amounts of the alkyl ketal ester favor lower values for y. Higher amounts of the hydroxyalkyl ketal ester favor lower values of y, and higher values of x and z and/or higher values of j and w.

When j or w is greater than 1 in formula II, some amount of self-condensation ("oligomerization") of the hydroxyalkyl ketal ester has taken place. In some embodiments of the formula II compound, $R^5$ is

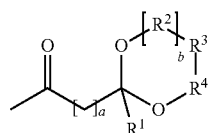

and (a) j=0, z is at least one and w is from 1 to 15, (b) z=0, x=1 and w is from 1 to 15 or (c), z=0, x is greater than 1 and w is from 1 to 15. In some other embodiments of the formula II compound, $R^5$ is hydrogen, j is from 0 to 15 and z is at least one. In some embodiments of the formula II compound, including those specific embodiments just mentioned, each Z is —O—.

In formula II, including the specific embodiments mentioned in the preceding paragraph, a and all e preferably are 2, all $R^1$ and $R^8$ preferably are methyl and $R^{14}$ is preferably an alkyl group, especially one having up to 4 carbon atoms. $R^6$ in any of the foregoing embodiments may include ether or ester groups.

Compounds according to formula II can be prepared in a transesterification reaction between the corresponding polyol, aminoalcohol or polyamine, the corresponding alkyl ketal ester and the corresponding hydroxyalkyl ketal ester. In some embodiments, all three of these materials are combined and reacted in a single step to form the formula II material. In other embodiments, the compound is formed in a one-pot process in which the reagents are added sequentially; in such a case the hydroxyalkyl ketal ester may be starve-fed to the reaction to minimize oligomerization. In other embodiments, the polyol, aminoalcohol or polyamine and hydroxyalkyl ketal ester are reacted first to form an intermediate, which is then reacted with the alkyl ketal ester. In still other embodiments, when the value of j and/or w in formula II is greater than 1, the hydroxyalkyl ketal ester can be oligomerized in a preliminary step, and the oligomerized material is then reacted with the other starting materials or with an intermediate formed by reaction of the polyol, aminoalcohol and/or polyamine and the alkyl ketal ester. Oligomerization of the hydroxyalkyl ketal ester also can be performed at the same time that the hydroxyalkyl ketal ester reacts with the other starting materials.

In formula I, n is preferably from 1 to 15, a and all c are preferably 2, $R^1$ and $R^8$ are preferably methyl and $R^{23}$ is preferably an alkyl or phenyl group. As with formula II, a value of n greater than 1 indicates that some oligomerization of the hydroxyalkyl ketal ester has occurred. n is more preferably from 1 to 2 and may be 1. The formula I compound is a 1:1 reaction product of the starting materials when n is 1.

Compounds according to formula I can be prepared in a transesterification reaction between the corresponding alkyl ketal ester and the corresponding hydroxyalkyl ketal ester. The values of n in formula I will depend on the relative number of moles of the alkyl ketal ester and hydroxyalkyl ketal ester, and the extent to which the reaction is continued. Higher amounts of the hydroxyalkyl ketal ester favor higher values of n. When n is greater than 1, indicating that the hydroxyalkyl ketal ester has oligomerized, it is possible to perform the oligomerization reaction separately, in a preliminary step. Alternatively, the oligomerization can be performed at the same time as the reaction with the alkyl ketal ester. If oligomerization is to be minimized or prevented, the hydroxyalkyl ketal ester may be starve-fed to the alkyl ketal ester under reaction conditions.

Compounds according to formula III correspond to reaction products of transesterification reaction between a full or partial polycarboxylic acid ester compound and one or more hydroxyalkyl ketal esters as described above.

The full or partial polycarboxylic acid ester compound is a material that contains more than one carboxyl group per molecule, at least one of which is esterified, preferably with a hydrocarbyl or substituted hydrocarbyl group having up to 12 carbon atoms, especially up to 6 carbon atoms. If all of the carboxyl groups are esterified, the polycarboxylic ester compound is said to be a full ester. A partial ester is one in which only a portion of the carboxyl groups are esterified; the remaining carboxyl groups may be in the acid or salt form. In some embodiments, the polycarboxylic acid ester may contain from 2 to 8 carboxylic acid or carboxylic acid groups, but preferably it contains from 2 to 4 such groups and more preferably is a monoester or a diester of a dicarboxylic acid.

The full or partial ester can be represented by the formula $R^{12}$—(COOX)$_n$, where $R^{12}$ is as defined before, n=1+s, and X is hydrocarbyl or substituted hydrocarbyl, hydrogen or a monovalent cation, further provided that at least one X is hydrocarbyl or substituted hydrocarbyl. It is preferred that all X are hydrocarbyl or substituted hydrocarbyl.

Examples of full or partial polycarboxylic acid esters suitable for forming the reaction product corresponding to III include monoesters and diesters of dicarboxylic acids in which $R^{12}$ is a covalent bond, divalent alkyl (especially those of the form —(CH2)$_k$— where k is from 1 to 20, especially 2 to 10), divalent alkenyl (especially the cis or trans form of —CH=CH—), divalent alkynyl, phenylene, substituted phenylene, and the like. Examples of suitable full or partial carboxylic acid esters include various esters of oxalic, malonic, adipic, sebacic, azelaic, maleic, fumaric, butandoic, succinic, dodecanoic and octadecandioic acids. In some embodiments, suitable diesters include diethyl adipate, diethyl sebacate, diethyl succinate, dimethyl adipate, dibutyl adipate, dioctyl adipate, dioctyl-phthalate, and butyl-benzyl phthalate.

Suitable hydroxyalkyl esters include those described above with respect to formula II.

In formula III, the values of w, s and v will depend on factors including the number of carboxylic acid or carboxylic acid ester groups on the full or partial carboxylic acid ester, the number of moles of hydroxyalkyl ketal ester per mole of the full or partial carboxylic acid ester, and the extent to which the reaction is taken towards completion. Higher amounts of the hydroxyalkyl ketal ester favor higher values of w, s and v. s is preferably from 1 to 7, more preferably from 1 to 3 and most preferably 1. w and v may each be from 1 to 100, preferably from 1 to 10. In some embodiments, w and v are each 1. In other embodiments, w+v is at least 3. In still other embodiments, v=0. When w=1, v=0 and s=1, the product corresponds to a 1:1 reaction product of the hydroxyalkyl ketal ester and a dicarboxylic acid mono- or diester. When w=v=s=1, the product corresponds to a 2:1 reaction product of the hydroxyalkyl ketal ester and a dicarboxylic acid mono- or diester. When either or both of w and v are greater than 1, the molecular weight of the formula III material may range from about 200 to 40,000 daltons, but is preferably from 300 to 3000 daltons.

In formula III, the value of each e is preferably 1 or 2, each $R^{14}$ is preferably methyl and each $R^{15}$ is preferably alkyl having up to 3 carbon atoms. Each $R^{10}$ is preferably C1-8 alkyl, more preferably C2-4 alkyl.

Compounds according to formula III can be prepared in a transesterification reaction between the corresponding full or partial polycarboxylic acid ester and the corresponding hydroxyalkyl ketal ester. In some embodiments, the materials are combined and reacted in a single step to form the formula III material. In other embodiments, when the value of n in formula III is greater than 1, the hydroxyalkyl ketal ester can be oligomerized in a preliminary step, and the oligomerized material is then reacted with the full or partial polycarboxylic acid ester. Oligomerization of the hydroxyalkyl ketal ester also can be performed at the same time that material reacts with the full or partial polycarboxylic acid ester. As before, oligomerization of the hydroxyalkyl ketal ester can be minimized or prevented by starve-feeding the material into the reaction under reaction conditions.

In some embodiments, a stoichiometric excess of hydroxyalkyl ketal ester is employed with respect to the full or partial polycarboxylic acid ester in order to form a reaction product having formula III. In some cases, about two equivalents of hydroxyalkyl ketal ester are employed per mole of carboxylate ester in one or more transesterification reactions. In other embodiments, greater than about 2 and up to 100 equivalents of hydroxyalkyl ketal ester are employed per equivalent of the polycarboxylic acid ester in the reaction to form compound IV. This mole ratio may be between about 2.1 to 50:1 or about 2.2-5:1. In still other embodiments, less than a 2:1 molar ratio of hydroxyalkyl ketal ester to full or partial polycarboxylic acid ester is used, although higher ratios can be used if the reaction is not taken to full conversion. In some other embodiments, where a 1:1 reaction product of the hydroxyalkyl ketal ester and the full or partial polycarboxylic acid ester is desired, about 1 to 10 equivalents of polycarboxylic acid ester is employed per mole of hydroxyalkyl ketal ester.

As before, a mixture of products is commonly obtained from the synthesis process. For example, it is common for the reaction product to contain a mixture of materials having various values of w, v and s. In some embodiments, a mixture of products is obtained, which includes species in which w and s are 1 and v is zero, as well as species in which w, s and v are all 1. In some embodiments, at least 75 wt. %, more preferably at least 85 wt. %, of such a mixture is the species in which w, s and v are all 1. In other embodiments, such a mixture contains no more than 10 wt. % or no more than 5 wt. % of the mixture is the species in which w, s and v are all 1.

Compounds according to formula IV can be prepared in a transesterification reaction between two hydroxyalkyl ketal acids or esters and a diol or polyol, wherein the polyoly can contain one or more heteroatoms. In some embodiments, the materials are combined and reacted in a single step to form the formula IV material. Generally an excess of the diol or polyol is provided to force the transesterification reaction to completion.

Certain compounds according to formulae I-IV may exist as optical and/or geometrical isomers. In such cases, any of the isomers are suitable.

The phrase "hydrocarbyl group" by itself or as part of another substituent refers to a saturated or unsaturated branched, straight-chain or cyclic monovalent hydrocarbon radical having the stated number of carbon atoms (i.e., C1-C6 means one to six carbon atoms) that is derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl," "alkenyl" and/or "alkynyl" is used, as defined below. "Lower alkyl" refers to alkyl groups having from 1 to 6 carbon atoms.

The term "hydrocarbyl" by itself or as part of another substituent refers to a saturated branched, straight-chain or cyclic alkyl derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

The term "hydrocarbenyl" by itself or as part of another substituent refers to an unsaturated branched, straight-chain or cyclic alkyl having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

In formulae I-IV herein, a "substituted" hydrocarbon or hydrocarbyl group may contain any substituents that do not react with carboxylate groups, hydroxyl groups or amino groups under the conditions of the reactions that form the various products of formulae I-IV. Therefore, the substituents should exclude groups such as hydroxyl, primary or secondary amino, mercapto, carboxylic acid or salts or esters thereof, carboxylic acid halides, sulfur- or phosphorus-containing acids, isocyanates and the like. In addition, the substituent groups also should not otherwise interfere with the reactions that form the various products of formulae I-IV. Suitable substituents include, carbonyl, halogen, tertiary amino, ether, sulfone and the like, among others.

The term "plasticizer" is known and refers to additives that increase the plasticity or fluidity of the material to which they are added. Plasticizers for plastics are additives, most commonly phthalates, that give hard plastics like PVC the desired flexibility and durability. They are often based on esters of polycarboxylic acids with linear or branched aliphatic alcohols of moderate chain length. Plasticizers work by embedding themselves between the chains of polymers, spacing them apart (increasing the "free volume"), and thus significantly lowering the glass transition temperature for the plastic and making it softer. For plastics such as PVC, the more plasticizer added, the lower its cold flex temperature will be. However, phthalates have been found to have adverse environmental as well as physiological effects. Advantageously, the plasticizers of the present invention do not suffer from these drawbacks.

Plasticizers according to formulae I-IV are prepared from renewable bio-based feedstocks, wherein "bio-based" is used as defined in ASTM D6866. As such, these compounds offer opportunities to replace petroleum-based products such as plasticizer with bio-based materials. Such a bio-based compounds can be blended with a bio-based organic polymer to form a polymer composition which is also bio-based. One such polymer is poly (lactic acid), or PLA.

The term "ketal" is recognized in the art and are useful chemical building blocks. These include cyclic ketals and acetals of oxocarboxylates with polyols. It is known, for example, that polyhydric alcohols, or polyols, having 1,2 and 1,3 hydroxy conformations can react with a ketone or aldehyde to form a cyclic ketal or an acetal (Carey, F. A. and Sundberg, R. J., "Advanced Organic Chemistry Part B: Reactions and Synthesis" 2nd ed., 1983, Plenum Press, NY, N.Y., p. 544).

Diols such as 1,2-ethane diol (ethylene glycol) and 1,3 propanediol (propylene glycol) are examples of such polyols. Diols having a 1,2 hydroxyl group configuration form dioxolanes when reacted with ketone or aldehyde moieties, while 1,3 diols form dioxanes.

Various ketals arising from the reaction of oxocarboxylic acids and esters thereof with diols and triols are known. Ono et al., J. Am. Oil Chem. Soc. 70(1), 29 (1993) disclose ketalization of ethyl pyruvate, ethyl acetoacetate, and ethyl levulinate with various 1-O-alkyl glycerols (diols). Okohara et al., JP1990000202989, similarly disclose ketalization of ethyl levulinate with 1-O-alkyl glycerols, followed by saponification of the ester moiety. McCullough et al., U.S. Pat. No. 5,998,092 disclose the ketalization of two keto acids with ethylene glycol. Chirila, Revistade Chimie 28(8), 730-3 (1977) discloses the 1:1 adduct of acetoacetate esters with glycerol. Gelas, Carbohydrate Research 30(1), 21-34 (1973) and Rakhmankulov et al., SU 722912 disclose the 1:1 adduct of pyruvate esters with glycerol and subsequent bicyclic lactone formation.

Ketals of glycerol and levulinic acid or an ester thereof are described in U.S. Patent Publication No. 2008/0242721, the entirety of which is incorporated herein by reference. The ketal reaction product of glycerol with a levulinate results in the ketal acid or ketal carboxylate, along with one mole of water per mole of ketal formed.

Levulinic acid, or 4-oxopentanoic acid, is an organic hydrocarbyl acid with the formula $CH_3C(O)CH_2CH_2CO_2H$.

Some examples of useful alkylketal ester starting materials include the 1,2-propane diol ketal of ethyl levulinate, the 1,3-propane diol ketal of propyl levulinate, 1,2-propane diol ketal of butyl levulinate, 1,3-propane diol ketal of ethyl levulinate and 1,2-ethane diol ketal of ethyl levulinate. Some examples of useful hydroxyalkyl ketal ester starting materials include the 1,2-glycerol ketal of methyl levulinate, 1,2-glycerol ketal of ethyl levulinate, 1,2-glycerol ketal of methyl acetoacetate, and 1,2-glycerol ketal of ethyl acetoacetate. Useful methods for making such alkyl ketal esters and hydroxyalkyl ketal esters are described in U.S. Patent Publication No. 2008/0242721 and International Patent Publication No. WO 2009/048874, which are incorporated herein by reference in their entirety.

The term "antioxidant" is recognized in the art and refers to a molecule capable of inhibiting the oxidation of other molecules. Oxidation is a chemical reaction that transfers electrons or hydrogen from a substance to an oxidizing agent. Oxidation reactions can produce free radicals. In turn, these radicals can start chain reactions which can degrade a material.

Suitable antioxidants include, for example, hindered phenols with an ester group, hindered phenol diamides, hindered phenols with an ether-ester linkage, hindered phenols with a hydrocarbyl ester linkage, hindered phenols, hindered amines, phosphites, alpha-beta unsaturated ketones, or mixtures thereof.

Exemplary antioxidant additives include organophosphites such as tris(nonyl phenyl)phosphite, tris(2,4-di-t-butylphenyl)phosphite, bis(2,4-di-t-butylphenyl)pentaerythritol diphosphite, distearyl pentaerythritol diphosphite, alkylated monophenols or polyphenols; alkylated reaction products of polyphenols with dienes, such as tetrakis[methylene(3,5-di-tert-butyl-4-hydroxyhydrocinnamate)] methane; butylated reaction products of para-cresol or dicyclopentadiene; alkylated hydroquinones; hydroxylated thiodiphenyl ethers; alkylidene-bisphenols; benzyl compounds; esters of beta-(3, 5-di-tert-butyl-4-hydroxyphenyl)-propionic acid with monohydric or polyhydric alcohols; esters of beta-(5-tert-butyl-4-hydroxy-3-methylphenyl)-propionic acid with monohydric or polyhydric alcohols; esters of thioalkyl or thioaryl compounds such as di stearylthiopropionate, dilaurylthiopropionate, ditridecylthiodipropionate, octadecyl-3-(3,5-di-tert-butyl-4-hydroxyphenyl)propionate, pentaerythrityl-tetrakis[3-(3,5-di-tert-butyl-4-hydroxyphenyl) propionate; amide of beta-(3,5-di-tert-butyl-4-hydroxyphenyl)-propionic acid, or combinations comprising at least one of the foregoing antioxidants. Antioxidants are generally used in amounts of 0.0001 to 5 parts by weight, based on 100 parts by weight of the plasticizer composition.

Exemplary heat stabilizer additives include organophosphites such as triphenyl phosphite, tris-(2,6-dimethylphenyl) phosphite, tris-(mixed mono- and di-nonylphenyl)phosphite; phosphonates such as dimethylbenzene phosphonate, phosphates such as trimethyl phosphate, or combinations comprising at least one of the foregoing heat stabilizers. Heat stabilizers are generally used in amounts of 0.0001 to 5 parts by weight, based on 100 parts by weight of the plasticizer composition.

Light stabilizers and/or ultraviolet light (UV) absorbing additives can also be used. Exemplary light stabilizer additives include benzotriazoles such as 2-(2-hydroxy-5-methylphenyl)benzotriazole, 2-(2-hydroxy-5-tert-octylphenyl)-benzotriazole and 2-hydroxy-4-n-octoxy benzophenone, or combinations comprising at least one of the foregoing light stabilizers. Light stabilizers are generally used in amounts of 0.0001 to 5 part by weight, based on 100 parts by weight of the plasticizer composition.

The term "UV absorber" (ultraviolet light absorber) is recognized in the art and is intended include molecules used in organic materials (polymers, paints, etc.) to absorb UV light to reduce the UV degradation (photo-oxidation) of a material. A number of different UVAs with different absorption properties exist. Examples include 2-hydroxyphenyl-benzophenone, a 2-(2-hydroxypeyl)-benzotriazole, a 2-hydroxyphenyl-s-triazine), ethanediamide, N-(2-ethoxyphenyl)-N'-(2-ethylphenyl)- or mixtures thereof.

Exemplary UV absorbing additives include hydroxybenzophenones; hydroxybenzotriazoles; hydroxybenzotriazines; cyanoacrylates; oxanilides; benzoxazinones; 2-(2H-benzotriazol-2-yl)-4-(1,1,3,3-tetramethylbutyl)-phenol (CYASORB® 5411); 2-hydroxy-4-n-octyloxybenzophenone (CYASORB® 531); 2-[4,6-bis(2,4-dimethylphenyl)-1, 3,5-triazin-2yl]5-(octyloxy)-pheno-1 (CYASORB® 1164); 2,2'-(1,4-phenylene)bis(4H-3,1-benzoxazin-4-one) (CYASORB® UV-3638); 1,3-bis[(2-cyano-3,3-diphenylacryloyl) oxy]-2,2-bis[[(2-cyano-3, 3-diphenylacryloyl)oxy]methyl] propane (UVINUL® 3030); 2,2'-(1,4-phenylene) bis(4H-3, 1-benzoxazin-4-one); 1,3-bis[(2-cyano-3,3-diphenylacryloyl)oxy]-2,2-bis[[(2-cyano-3,3-diphenyl-acryloyl)oxy]methyl]propane; nano-size inorganic materials such as titanium oxide, cerium oxide, and zinc oxide, all with particle size less than or equal to about 100 nanometers; or combinations comprising at least one of the foregoing UV absorbers. UV absorbers are generally used in amounts of 0.0001 to 10 parts by weight, based on 100 parts by weight of the plasticizer composition.

Other suitable UV absorbers include, for example, benzophenones, such as CYASORB UV-9 (2-hydroxy-4-methoxybenzophenone, CHIMASSORB 81 (or CYASORB UV 531) (2 hydroxy-4 octyloxybenzophenone).

TINUVIN P, TINUVIN 234, TINUVIN 326, TINUVIN 328, CYASORB UV 5411 and CYASORB UV 237 are suitable examples of benzotriazoles.

CYASORB UV 1164 (2-[4,6-bis(2,4-dimethylphenyl)-1, 3,5-triazin-2yl]-5(oxctyloxy) phenol is an exemplary triazine UV absorber. CYASORB 3638 is a suitable UV absorber which is a benzoxazinone.

In addition, hindered amine light stabilizers (HALS) are extremely efficient stabilizers against light-induced degradation of most polymers. They do not generally absorb UV radiation, but act to inhibit degradation of the polymer. These are typically tetra alkyl piperidines, such as 2,2,6,6-tetramethyl-4-piperidinamine and 2,2,6,6-tetramethyl-4-piperidinol.

The phrase "thermal stabilizer" is recognized in the art and refers to materials that prevent various effects such as oxidation, chain scission and uncontrolled recombinations and cross-linking reactions that are caused by oxidation of polymers.

Suitable examples of thermal stabilizers include Group I or Group II metal stearates, such as sodium or calcium stearate.

The plasticizer compositions described herein include from about 0.01 to about 5.0 percent by weight of the total composition of an antioxidant, a UV stabilizer, a thermal stabilizer or mixtures thereof. Exemplary amounts include 0.02, 0.05, 0.1, 0.2, 0.5, 1.0, 1.5, 2.0, and all amounts between 0.01 and 5.0.

The plasticizers described herein have a molecular weight of greater than 300. In some embodiments, the molecular is about 500, more particularly about 1000 and even more particularly about 2000.

The plasticizers described herein have a color index (YI) of less than 50 as measured by ASTM method E313. In particular, the YI index is less than 20, less than 15, less than 10, less than 5 and most particularly, less than 1 as measured by ASTM method E313.

The plasticizers described herein have a mass loss of less than 2% after 10 days at 110° C. and less than 15% relative humidity (RH).

A process for plasticizing a polymer is also provided that includes melt or solution blending a polymer and a plasticizing amount of at least one compound of formula I, at least one compound of formula II, at least compound of formula III, at least one compound of formula IV or a mixture of two or more of compounds having formulae I, II, III IV or V.

Plasticizers according to formulae I through IV can be prepared in a transesterification or ester-aminolysis reaction between the corresponding polyol, aminoalcohol or polyamine and the corresponding alkyl ketal ester. Alternatively, compounds according to formula I can be prepared by reacting an oxocarboxylic acid with the polyol, aminoalcohol or polyamine to form an ester or amide, and then ketalizing the resulting product with a 1,2- or 1,3-alkane diol such as ethylene glycol, 1,2-propanediol, 1,3-propanediol, 1,2-butanediol, 1,3-butanediol, 1,2-pentanediol, 1,3-pentanediol, 1,2-hexanediol, 1,3-hexanediol, and the like. Ketalization is conveniently performed according to the methods described in International Patent Publication No. WO 2009/048874, or U.S. Patent Publication No. 2008/0242721.

A mixture of products is commonly obtained from the synthesis process. For example, it is common for the reaction product to contain a mixture of materials having various values of x and y. It is preferred that no more than 25 mole percent of the product represents compounds in which y is 1 or greater. In especially preferred cases in which the starting polyol is a diol, it is preferred that at least 75 mole of the product is species in which x is 2 and y is zero.

The synthetic procedures described herein provide the plasticizers with a purity of at least 90%. This has not been possible prior to the invention as unwanted side products/by products were produced. In particular, the purity of the plasticizers are 91%, 92%, etc. through 100%. The term purity reflects the selectivity of producing a particular component from the reaction mixture, such as compound of formula 2, noted below. That is, the reaction selectively provides a compound, such as formula, in at least 90% selectivity with a minimal amount of undesired side products.

Processes are provided herein to prepare the plasticizers described throughout. For example, a process is provided to prepare a plasticizer comprising at least 2 alkyl ketal ester moieties with a molecular weight of greater than 300, comprising the step of contacting under reaction conditions an alkyl ketal ester having an acid number less than 0.3 as determined by ASTM method ASTM D664, a multihydric hydrocarbyl moiety, or a monohydric alkyl ketal ester; and a catalyst, wherein a plasticizer comprising at least 2 alkyl ketal ester moieties is obtained with a molecular weight of greater than 300.

A process is provided to prepare a plasticizer described herein in at least a 90% purity, wherein the plasticizer has a molecular weight of greater than 300 with at least 2 alkyl ketal ester moieties. The process includes the step of contacting under reaction conditions, an alkyl ketal ester, a multihydric hydrocarbyl moiety, or a monohydric alkyl ketal ester; a catalyst; and an antioxidant, a thermal stabilizer or mixtures thereof, wherein a plasticizer comprising at least 2 alkyl ketal ester moieties is obtained with a molecular weight of greater than 300 and is produced in at least a 90% selectivity of the intended product.

Another process is provided to prepare a plasticizer described herein, wherein the plasticizer has a molecular weight of greater than 300 with at least 2 alkyl ketal ester moieties, including the step of contacting under reaction conditions an alkyl ketal ester, a multihydric hydrocarbyl moiety, or a monohydric alkyl ketal ester; a catalyst; and an adsorbent, carbon, alumina, a buffer solution, a basic solution or mixtures thereof, wherein a plasticizer comprising at least 2 alkyl ketal ester moieties with a molecular weight of greater than 300 is obtained.

A further process is provided to prepare a plasticizer described herein, wherein the plasticizer comprises at least 2 alkyl ketal ester moieties with a molecular weight of greater than 300. The process includes the step of contacting an alkyl ketal ester, a multihydric hydrocarbyl moiety, or a monohydric alkyl ketal ester; a catalyst; and, optionally, an antioxidant under reaction conditions, wherein the reaction is conducted under an inert gas, such as nitrogen or argon or under vacuum, providing a plasticizer that has a color index (YI) of less than 50 measured by ASTM method E313 having at least 2 alkyl ketal ester moieties with a molecular weight of greater than 300.

Another process is provided to prepare a plasticizer as described herein, wherein the plasticizer comprises at least 2 alkyl ketal ester moieties with a molecular weight of greater than 300. The process includes the step of contacting i) the plasticizer having a molecular weight of greater than 300 and at least 2 alkyl ketal ester moieties with ii) hydrogen under hydrogenation conditions to provide a purified plasticizer that has a color index (YI) of less than 50 measured by ASTM method E313 and having at least 2 alkyl ketal ester moieties with a molecular weight of greater than 300.

With regard to the processes described herein, in one aspect, the starting alkyl ketal ester has an acid number less than 0.2, more particularly less than 0.15.

Suitable catalysts include metal alkoxides. It has been found that use of metal alkoxides helps to provide a plasticizer that has an acid number less than 0.3. As such, the production of unwanted by products/degradation products are minimized or eliminated. While the choice of catalyst employed in the reactions is not particularly limited within the scope of the disclosure, a preferred set of embodiments employs metallic catalysts, for example, a catalyst based on titanium, aluminum, zirconium, or tin, such as titanium tetraisopropoxide (Ti(O$^i$Pr)4), or tin (II) octanoate, tin (II) alkoxides, dialkyltin alkoxides, or organic zirconates. Other suitable catalysts are, for example, organic titanates and zirconates marketed under Tyzor® brand by DuPont deNemours and Co. of Wilmington, Del. In some embodiments, more than one species of catalyst is used; thus, blends of one or more catalysts such as those mentioned above may be used in a mixture to catalyze the formation of compounds of formulae I-IV.

In one embodiment, the metal ion is titanium and a suitable catalyst is titanium isopropoxide.

The transesterification reactions that are used to form the compounds of formulae I-IV can be carried out in the presence of an inert solvent, such as hexane, toluene, dichlorobenzene and the like. In other embodiments the reaction is carried out neat. In some embodiments, the reaction is performed at temperature and pressure conditions such that the condensation coproduct, i.e., an alcohol in most cases but water in some cases, evaporates from the reaction mixture, wherein the vapor is condensed and thereby removed. In some embodiments, a temperature between about 60° C. and 300° C. is employed; in other embodiments, a temperature of about 100° C. to 250° C. is employed; in still other embodiments, a temperature of about 160° C. to 240° C. is employed to accomplish the reaction. In some embodiments, pressure in the reaction vessel is lowered to below atmospheric pressure to assist in the removal of the condensation by-product, i.e., the alcohol or water. In some embodiments, nitrogen is sparged or swept through the reaction mixture to assist in the removal of the coproduct alcohol.

Generally the process is conducted at a temperature range of from about 150° C. to about 250° C.

Suitable adsorbents include, for example, carbon, alumina, a buffer solution, a basic solution, calcium oxide or mixtures thereof.

Suitable hydrogenation catalysts include, for example, heterogeneous metal catalysts like nickel, palladium, platinum, ruthenium, copper, and the like. The catalysts may be supported onto carbon, alumina, or silica. Homogeneous catalysts may also be used with the above metals, modified with the appropriate organic ligands in order to form a soluble species. Exemplary embodiments include, 5% Palladium on Carbon (Escat 147, Escat 142), 10% Palladium on Carbon, Copper Chromite, BASF Ni 5249 P, 5% Ruthenium on Carbon (Escat 440)

Antioxidants, UV stabilizers and thermal stabilizers, useful in the processes described herein are as noted throughout the specification. Similarly, color index values (YI) for products obtained by the processes described herein are as noted throughout the specification.

The various synthesis reactions described herein can be carried out batch wise or in continuous mode, depending on equipment, scale, and other reaction parameters. The reaction vessel may be made of any suitable material. In some embodiments, the reagents are dried before addition of catalyst, using any convenient technique. In embodiments, drying is accomplished by warming the reaction vessel to about 60° C.-110° C. and applying a vacuum of 5-20 Torr for at least about an hour; in other embodiments a dry inert gas, such as nitrogen or argon, is swept continuously through the vessel instead of applying a vacuum. The reagents are, in some embodiments, analyzed for water content prior to addition of catalyst to the vessel. In other embodiments, the reagents are dried separately prior to addition to the reaction vessel and are introduced to the vessel by a closed system, such as by pipes or tubes, which does not entrain water or air during introduction of the reagents to the vessel.

The catalyst may be added batchwise or in continuous fashion to the vessel. In embodiments, during the addition of catalyst, the reagents are at the same temperature as employed during drying. In other embodiments the reagents are preheated to a targeted temperature, for example in the ranges specified above, prior to addition of the catalyst. After catalyst addition, in some embodiments, a vacuum is employed to remove any air that has become entrained during the addition. In other embodiments, the catalyst is introduced to the vessel by a closed system, such as by pipes or tubes that do not entrain water or air during introduction of the reagents to the vessel. The reaction is, in embodiments, carried out under an inert gas blanket or an inert gas sparge, and agitated using any convenient means of agitation.

In embodiments, the reaction is complete in less than about 2 hours; in other embodiments the reaction is complete between about 1 hour and 12 hours; in still other embodiments the reaction is complete in about 2 to 8 hours. In some embodiments, the limiting reagent in the reaction is metered in gradually by employing an addition funnel, metered pump, or another apparatus known in the industry. Metering of a reagent is, in embodiments, initiated after or during addition of the catalyst and is particularly useful where the reaction is accomplished in a continuous process.

Compounds according to formulae I-IV often perform a plasticizing function when blended with organic polymers. When a compound of formulae I-IV is to perform such a function, it is preferably liquid at room temperature or, if a solid at room temperature, it has a glass transition temperature and/or softening temperature below room temperature, often 0° or −20° C. Plasticization is indicated by a reduction in $T_g$ of the composition, compared to that of the neat organic polymer, and or a softening or flexibilizing effect, as indicated by a reduction in Shore hardness and/or a lowered flexural modulus, respectively. Typically, the combination the organic polymer and the compound of any of formulae I-IV will have a $T_g$ of at least 5° C. lower at least 15° C. lower, at least 30° C. lower, or at least 50° C. lower than a $T_g$ of the neat polymer, as measured by DSC according to ASTM D3418 or other DSC method. A useful general procedure is as follows: The sample is evaluated on a TA Q200 instrument with refrigerated cooling and TA Thermal Advantage software (TA Instruments; New Castle, Del.), or equivalent, using a ramp rate of 20° C./min. Samples are ramped from room temperature to 210° C. followed by a rapid quench. Samples are then reheated to 210° C. at a rate of 20° C./min. Glass transition temperature is measured on the second scan.

When used to perform a plasticizing function, a compound of any of formulae I-IV preferably have viscosities less than about 500 centipoise (cP) at 25° C. The viscosity may be from about 1 cP to 250 cP; or about 50 cP to 200 cP at 25° C. Low viscosity provides ease of compounding into one or more polymer compositions without, for example, preheating or addition of diluents or solvents to lower viscosity and enables the creation of pastes such as plastisols.

The following paragraphs enumerated consecutively from 1 through 163 provide for various aspects of the present invention. In one embodiment, in a first paragraph (1), the present invention provides a composition comprising a plasticizer comprising at least 2 alkyl ketal ester moieties and having a molecular weight of greater than 300; and at least one of an antioxidant, a UV stabilizer, a thermal stabilizer or mixtures thereof, present in the composition from about 0.01 to about 5.0 percent by weight of the total composition.

2. The composition of paragraph 1, wherein the alkyl ketal ester moieties are levulinic ester ketals.

3. The composition of either of paragraphs 1 or 2, wherein the plasticizer comprises a formula of:

or combinations thereof, wherein each a, independently, is from 0 or an integer of 1 to 12;
each b, independently, is 0 or 1;
c is from 0 to 12;
d is 0 or 1;
each e, independently, is from 0 to 12;
each f, independently, is from 0 to 12;
each i is 0 or 1;
each j, independently, is 0 to 100;
each $R^1$, independently, is a hydrogen, a hydrocarbyl group, or a substituted hydrocarbyl group;
each $R^2$, $R^3$ and $R^4$ are independently methylene, alkylmethylene, or dialkylmethylene;
$R^5$ is a hydrogen or

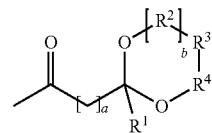

$R^6$ is a hydrocarbyl group or a substituted hydrocarbyl group;
each $R^7$, independently, is a hydrogen, a hydrocarbyl or a substituted hydrocarbyl group;
each $R^8$, independently, is a hydrogen, a hydrocarbyl or a substituted hydrocarbyl group;
each $R^{10}$, independently, is a hydrocarbyl or a substituted hydrocarbyl group;

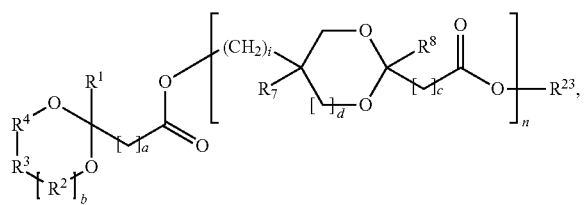

(I)

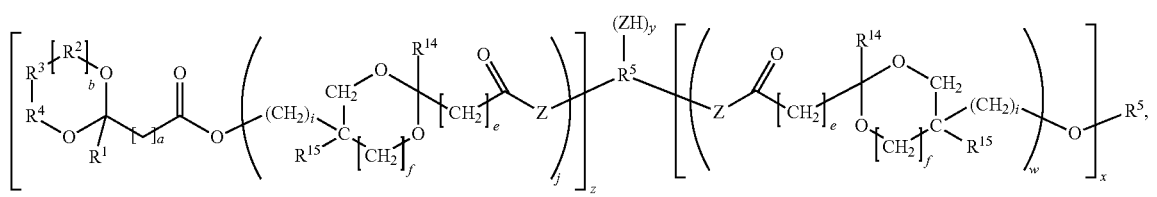

(II)

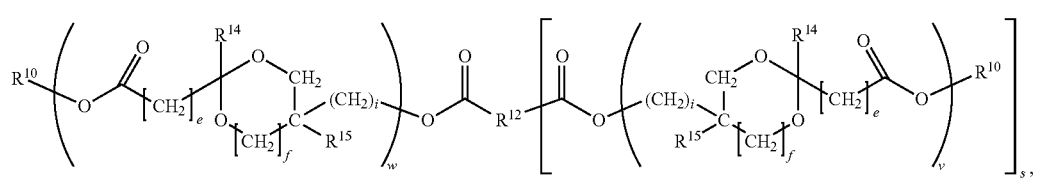

(III)

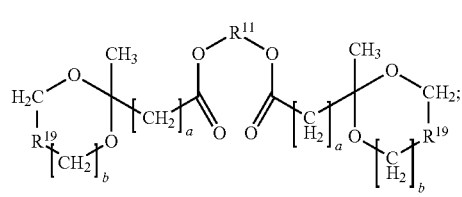

(IV)

$R^{11}$ is a hydrocarbyl, a substituted hydrocarbyl, or a hydrocarbyl group terminated with one or more heteroatoms to form a cyclic membered ring and which can include one or more of —O—, —NH—, —NR—, wherein R is a hydrocarbyl or a substituted hydrocarbyl;

$R^{12}$, is a covalent bond, a hydrocarbyl group or a substituted hydrocarbyl group;

each $R^{14}$, independently, is a hydrogen, a hydrocarbyl, or a substituted hydrocarbyl group;

each $R^{15}$, independently, is a hydrogen, a hydrocarbyl, or a substituted hydrocarbyl group;

each $R^{19}$, independently, is a hydrocarbyl, a substituted hydrocarbyl, or a hydrocarbyl group substituted with up to 5 hydroxyl groups;

each $R^{23}$ is a hydrocarbyl group or substituted hydrocarbyl group having between 1 and 12 carbon atoms each Z, independently, is —O—, —NH— or —NR— where R is a hydrocarbyl or a substituted hydrocarbyl group;

n is from 1 to 100;

s is at least one;

v is from 0 to 100;

w is from 1 to 100;

x is at least 1;

y is 0 or a positive number; and z is 0 or a positive number provided that z is at least one when $R^5$ is hydrogen.

4. The composition of any of paragraphs 1 through 3, wherein the plasticizer is the compound of formula (I) wherein b is 0, i is 1, $R^1$ is a hydrocarbyl, $R^3$ is an alkylmethylene, $R^4$ is a methylene, $R^7$ is a H, $R^8$ is a hydrocarbyl group, $R^{23}$ is a hydrocarbyl group, c is 2, d is 0 and n=1.

5. The composition of paragraph 4, wherein b is 0, i is 1, $R^1$ is a methyl group, $R^3$ is $CH_3CH$, $R^4$ is a methylene, $R^7$ is a H, $R^8$ is a methyl group, $R^{23}$ is an ethyl group, c is 2, d is 0 and n=1.

6. The composition of any of paragraphs 1 through 3, wherein the plasticizer is the compound of formula (IV) wherein $R^{11}$ is a C4 alkyl.

7. The composition of paragraph 6, wherein each a=2 and each b=0.

8. The composition of any of paragraphs 1 through 7, wherein the antioxidant is a hindered phenol with an ester group, a hindered phenol diamide, a hindered phenol with an ether-ester linkage, a hindered phenol with a hydrocarbyl ester linkage, a hindered phenol, a hindered amine, a phosphite, an alpha-beta unsaturated ketone, or mixtures thereof.

9. The composition of paragraph 1, wherein the antioxidant is a hindered phenol.

10. The composition of paragraph 9, wherein the antioxidant is a hindered phenol with an ester group.

11. The composition of any of paragraphs 1 through 7, wherein the UV stabilizer is a 2-hydroxyphenyl-benzophenone, a 2-(2-hydroxypeyl)-benzotriazole, a 2-hydroxyphenyl-s-triazine), or mixtures thereof.

12. The composition of paragraph 11, wherein the UV stabilizer is ethanediamide, N-(2-ethoxyphenyl)-N'-(2-ethylphenyl)-.

13. The composition of any of paragraphs 1 through 7, wherein the thermal stabilizer is a Group I or Group II metal stearate.

14. The composition of paragraph 13, wherein the thermal stabilizer is sodium or calcium stearate.

15. The composition of any of paragraphs 1 through 14, having a color index (YI) of less than 50 measured by ASTM method E313.

16. The composition of any of paragraphs 1 through 14, having a color index (YI) of less than 20 measured by ASTM method E313.

17. The composition of any of paragraphs 1 through 14, having a color index (YI) of less than 5 measured by ASTM method E313.

18. The composition of any of paragraphs 1 through 14, having a color index (YI) of less than 1 measured by ASTM method E313.

19. The composition of any of paragraphs 1 through 18, wherein the mass loss is less than 2% after 10 days at 110° C. and less than 15% RH.

20. A plasticizer comprising at least 2 alkyl ketal ester moieties, the plasticizer having a molecular weight of greater than 300 comprising a formula of:

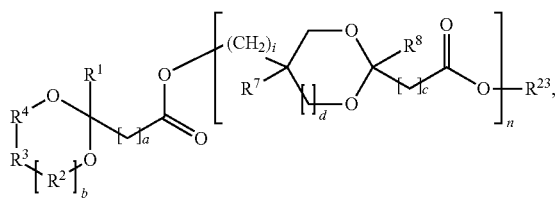

(I)

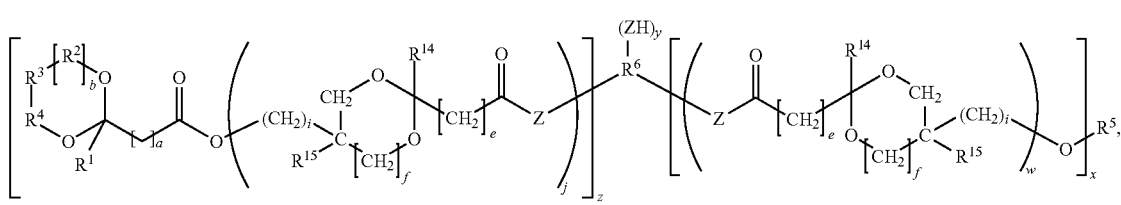

(II)

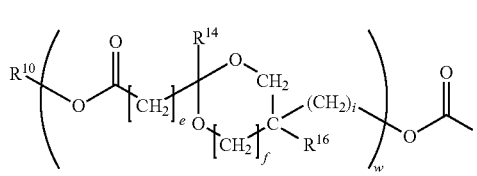

(III)

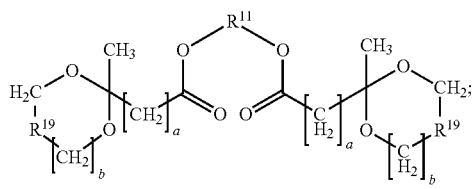

(IV)

or combinations thereof, wherein each a, independently, is from 0 or an integer of 1 to 12;
each b, independently, is 0 or 1;
c is from 0 to 12;
d is 0 or 1;
each e, independently, is from 0 to 12;
each f, independently, is from 0 to 12;
each i is 0 or 1;
each j, independently, is 0 to 100;
each $R^1$, independently, is a hydrogen, a hydrocarbyl group, or a substituted hydrocarbyl group;
each $R^2$, $R^3$ and $R^4$ are independently methylene, alkylmethylene, or dialkylmethylene;
$R^5$ is a hydrogen or

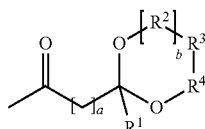

$R^6$ is a hydrocarbyl group or a substituted hydrocarbyl group;
each $R^7$, independently, is a hydrogen, a hydrocarbyl or a substituted hydrocarbyl group;
each $R^8$, independently, is a hydrogen, a hydrocarbyl or a substituted hydrocarbyl group;
each $R^{10}$, independently, is a hydrocarbyl or a substituted hydrocarbyl group;
$R^{11}$ is a hydrocarbyl, a substituted hydrocarbyl, or a hydrocarbyl group terminated with one or more heteroatoms to form a cyclic membered ring and which can include one or more of —O—, —NH—, —NR—, wherein R is a hydrocarbyl or a substituted hydrocarbyl;
$R^{12}$, is a covalent bond, a hydrocarbyl group or a substituted hydrocarbyl group;
each $R^{14}$, independently, is a hydrogen, a hydrocarbyl, or a substituted hydrocarbyl group;
each $R^{15}$, independently, is a hydrogen, a hydrocarbyl, or a substituted hydrocarbyl group;
each $R^{19}$, independently, is a hydrocarbyl, a substituted hydrocarbyl, or a hydrocarbyl group substituted with up to 5 hydroxyl groups;
each $R^{23}$ is a hydrocarbyl group or substituted hydrocarbyl group having between 1 and 12 carbon atoms each Z, independently, is —O—, —NH— or —NR— where R is a hydrocarbyl or a substituted hydrocarbyl group;
n is from 1 to 100;
s is at least one;
v is from 0 to 100;
w is from 1 to 100;
x is at least 1;
y is 0 or a positive number; and
z is 0 or a positive number provided that z is at least one when $R^5$ is hydrogen, wherein the plasticizer has a color index (YI) of less than 50 measured by ASTM method E313 and has a purity of at least 90%.

21. The plasticizer of paragraph 20, wherein the plasticizer is the compound of formula (I) wherein b is 0, i is 1, $R^1$ is a hydrocarbyl, $R^3$ is an alkylmethylene, $R^4$ is a methylene, $R^7$ is a H, $R^8$ is a hydrocarbyl group, $R^{23}$ is a hydrocarbyl group, c is 2, d is 0 and n=1.

22. The plasticizer of paragraph 21, wherein b is 0, i is 1, $R^1$ is a methyl group, $R^3$ is $CH_3CH$, $R^4$ is a methylene, $R^7$ is a H, $R^8$ is a methyl group, $R^{23}$ is an ethyl group, c is 2, d is 0 and n=1.

23. The plasticizer of paragraph 20, wherein the plasticizer is the compound of formula (IV) wherein $R^{11}$ is a C4 alkyl.

24. The plasticizer of paragraph 23, wherein each a=2 and each b=0.

25. The plasticizer of any of paragraphs 20 through 23, wherein the color index (YI) is less than 50 measured by ASTM method E313.

26. The plasticizer of any of paragraphs 20 through 23, wherein the color index (YI) is less than 30 measured by ASTM method E313.

27. The plasticizer of any of paragraphs 20 through 24, wherein the color index (YI) is less than 20 measured by ASTM method E313.

28. The plasticizer of any of paragraphs 20 through 24, wherein the color index (YI) is less than 15 measured by ASTM method E313.

29. The plasticizer of any of paragraphs 20 through 24, wherein the color index (YI) is less than 1 measured by ASTM method E313.

30. The plasticizer of any of paragraphs 20 through 29, wherein the mass loss is less than 2% after 10 days at 110° C. and less than 15% RH.

31. A plasticizer comprising at least 2 alkyl ketal ester moieties, the plasticizer having a molecular weight of greater than 300 comprising a formula of:

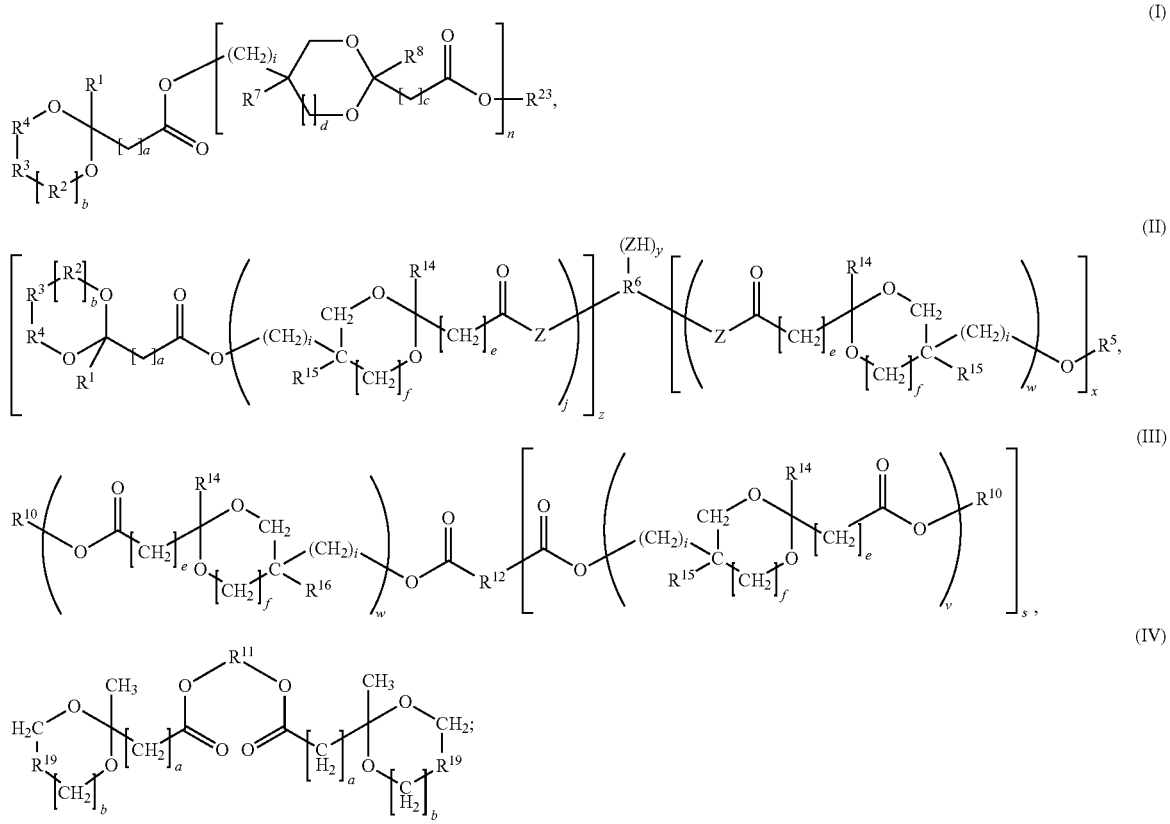

or combinations thereof, wherein each a, independently, is from 0 or an integer of 1 to 12;
each b, independently, is 0 or 1;
c is from 0 to 12;
d is 0 or 1;
each e, independently, is from 0 to 12;
each f, independently, is from 0 to 12;
each i is 0 or 1;
each j, independently, is 0 to 100;
each $R^1$, independently, is a hydrogen, a hydrocarbyl group, or a substituted hydrocarbyl group;
each $R^2$, $R^3$ and $R^4$ are independently methylene, alkylmethylene, or dialkylmethylene;
$R^5$ is a hydrogen or

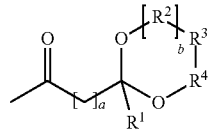

$R^6$ is a hydrocarbyl group or a substituted hydrocarbyl group;
each $R^7$, independently, is a hydrogen, a hydrocarbyl or a substituted hydrocarbyl group;
each $R^8$, independently, is a hydrogen, a hydrocarbyl or a substituted hydrocarbyl group;
each $R^{10}$, independently, is a hydrocarbyl or a substituted hydrocarbyl group;

$R^{11}$ is a hydrocarbyl, a substituted hydrocarbyl, or a hydrocarbyl group terminated with one or more heteroatoms to form a cyclic membered ring and which can include one or more of —O—, —NH—, —NR—, wherein R is a hydrocarbyl or a substituted hydrocarbyl;
$R^{12}$, is a covalent bond, a hydrocarbyl group or a substituted hydrocarbyl group;
each $R^{14}$, independently, is a hydrogen, a hydrocarbyl, or a substituted hydrocarbyl group;
each $R^{15}$, independently, is a hydrogen, a hydrocarbyl, or a substituted hydrocarbyl group;
each $R^{19}$, independently, is a hydrocarbyl, a substituted hydrocarbyl, or a hydrocarbyl group substituted with up to 5 hydroxyl groups;
each $R^{23}$ is a hydrocarbyl group or substituted hydrocarbyl group having between 1 and 12 carbon atoms
each Z, independently, is —O—, —NH— or —NR— where R is a hydrocarbyl or a substituted hydrocarbyl group;
n is from 1 to 100;
s is at least one;
v is from 0 to 100;
w is from 1 to 100;
x is at least 1;
y is 0 or a positive number; and
z is 0 or a positive number provided that z is at least one when $R^5$ is hydrogen, wherein the mass loss is less than 2% after 10 days at 110° C. and less than 15% RH.

32. The plasticizer of paragraph 31, wherein the plasticizer is the compound of formula (I) wherein b is 0, i is 1, $R^1$ is a hydrocarbyl, $R^3$ is an alkylmethylene, $R^4$ is a methylene, $R^7$ is a H, $R^8$ is a hydrocarbyl group, $R^{23}$ is a hydrocarbyl group, c is 2, d is 0 and n=1.

33. The plasticizer of paragraph 32, wherein b is 0, i is 1, $R^1$ is a methyl group, $R^3$ is $CH_3CH$, $R^4$ is a methylene, $R^7$ is a H, $R^8$ is a methyl group, $R^{23}$ is an ethyl group, c is 2, d is 0 and n=1.

34. The plasticizer of paragraph 31, wherein the plasticizer is the compound of formula (IV) wherein $R^{11}$ is a C4 alkyl.

35. The plasticizer of paragraph 34, wherein each a=2 and each b=0.

36. The plasticizer of any of paragraphs 31 through 35, wherein the color index (YI) is less than 50 measured by ASTM method E313.

37. The plasticizer of any of paragraphs 31 through 35, wherein the color index (YI) is less than 20 measured by ASTM method E313.

38. The plasticizer of any of paragraphs 31 through 35, wherein the color index (YI) is less than 5 measured by ASTM method E313.

39. The plasticizer of any of paragraphs 31 through 35, wherein the color index (YI) is less than 1 measured by ASTM method E313.

40. A process to prepare a plasticizer comprising at least 2 alkyl ketal ester moieties, the plasticizer having a molecular weight of greater than 300, comprising the step: contacting under reaction conditions an alkyl ketal ester having an acid number less than 0.3 as determined by ASTM method D664, a multihydric hydrocarbyl moiety, or a monohydric alkyl ketal ester; and a catalyst, wherein a plasticizer comprising at least 2 alkyl ketal ester moieties is obtained with a molecular weight of greater than 300.

41. The process of paragraph 40, wherein the alkyl ketal ester has an acid number less than 0.2.

42. The process of paragraph 40, wherein the alkyl ketal ester has an acid number less than 0.15.

43. The process of any of paragraphs 40 through 42, wherein the catalyst is a metal alkoxide.

44. The process of paragraph 43, wherein the metal ion is titanium.

45. The process of paragraph 43, wherein the metal alkoxide is titanium isopropoxide.

46. The process of any of claims 40 through 45, wherein the process is conducted at a temperature range of from about 150° C. to about 250° C.

47. The process of any of paragraphs 40 through 46, wherein the plasticizer has a color index (YI) of less than 50 measured by ASTM method E313.

48. The process of any of paragraphs 40 through 46, wherein the plasticizer has a color index (YI) of less than 20 measured by ASTM method E313.

49. The process of any of paragraphs 40 through 46, wherein the plasticizer has a color index (YI) of less than 5 measured by ASTM method E313.

50. The process of any of paragraphs 40 through 46, wherein the plasticizer has a color index (YI) of less than 1 measured by ASTM method E313.

51. The process of any of paragraphs 40 through 50, wherein the plasticizer has a formula comprising:

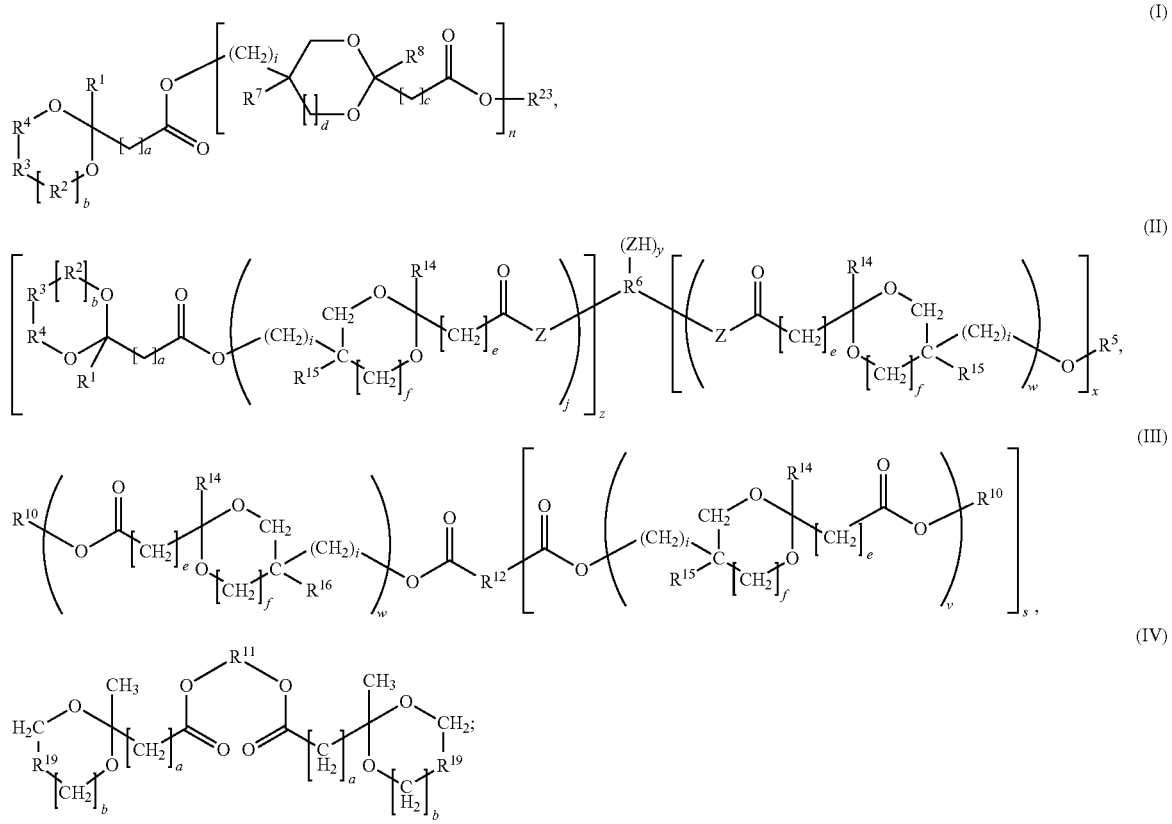

or combinations thereof, wherein each a, independently, is from 0 or an integer of 1 to 12;

each b, independently, is 0 or 1;

c is from 0 to 12;
d is 0 or 1;
each e, independently, is from 0 to 12;
each f, independently, is from 0 to 12;
each i is 0 or 1;
each j, independently, is 0 to 100;
each $R^1$, independently, is a hydrogen, a hydrocarbyl group, or a substituted hydrocarbyl group;
each $R^2$, $R^3$ and $R^4$ are independently methylene, alkylmethylene, or dialkylmethylene;
$R^5$ is a hydrogen or

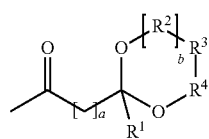

$R^6$ is a hydrocarbyl group or a substituted hydrocarbyl group;
each $R^7$, independently, is a hydrogen, a hydrocarbyl or a substituted hydrocarbyl group;
each $R^8$, independently, is a hydrogen, a hydrocarbyl or a substituted hydrocarbyl group;
each $R^{10}$, independently, is a hydrocarbyl or a substituted hydrocarbyl group;
$R^{11}$ is a hydrocarbyl, a substituted hydrocarbyl, or a hydrocarbyl group terminated with one or more heteroatoms to form a cyclic membered ring and which can include one or more of —O—, —NH—, —NR—, wherein R is a hydrocarbyl or a substituted hydrocarbyl;
$R^{12}$, is a covalent bond, a hydrocarbyl group or a substituted hydrocarbyl group;
each $R^{14}$, independently, is a hydrogen, a hydrocarbyl, or a substituted hydrocarbyl group;
each $R^{15}$, independently, is a hydrogen, a hydrocarbyl, or a substituted hydrocarbyl group;
each $R^{19}$, independently, is a hydrocarbyl, a substituted hydrocarbyl, or a hydrocarbyl group substituted with up to 5 hydroxyl groups;
each $R^{23}$ is a hydrocarbyl group or substituted hydrocarbyl group having between 1 and 12 carbon atoms
each Z, independently, is —O—, —NH— or —NR— where R is a hydrocarbyl or a substituted hydrocarbyl group;
n is from 1 to 100;
s is at least one;
v is from 0 to 100;
w is from 1 to 100;
x is at least 1;
y is 0 or a positive number.

52. The process of paragraph 51, wherein the plasticizer is the compound of formula (I) wherein b is 0, i is 1, $R^1$ is a hydrocarbyl, $R^3$ is an alkylmethylene, $R^4$ is a methylene, $R^7$ is a H, $R^8$ is a hydrocarbyl group, $R^{23}$ is a hydrocarbyl group, c is 2, d is 0 and n=1.

53. The process of paragraph 52, wherein b is 0, i is 1, $R^1$ is a methyl group, $R^3$ is $CH_3CH$, $R^4$ is a methylene, $R^7$ is a H, $R^8$ is a methyl group, $R^{23}$ is an ethyl group, c is 2, d is 0 and n=1.

54. The process of paragraph 51, wherein the plasticizer is the compound of formula (IV) wherein $R^{11}$ is a C4 alkyl.

55. The process of paragraph 54, wherein each a=2 and each b=0.

56. The process of any of paragraphs 40 through 55, wherein the mass loss of the plasticizer is less than 2% after 10 days at 110° C. and less than 15% RH.

57. A process to prepare a plasticizer in at least a 90% yield, wherein the plasticizer has a molecular weight of greater than 300 with at least 2 alkyl ketal ester moieties, comprising the step: contacting under reaction conditions, an alkyl ketal ester, a multihydric hydrocarbyl moiety, or a monohydric alkyl ketal ester; a catalyst; and an antioxidant, a thermal stabilizer or mixtures thereof, wherein a plasticizer comprising at least 2 alkyl ketal ester moieties is obtained with a molecular weight of greater than 300 and is produced in at least a 90% yield.

58. The process of paragraph 57, wherein the plasticizer has a formula comprising:

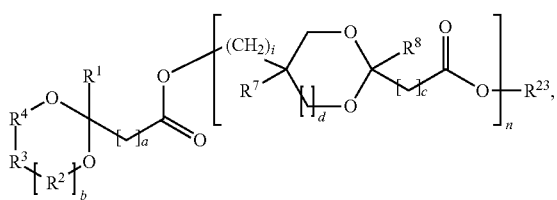

(I)

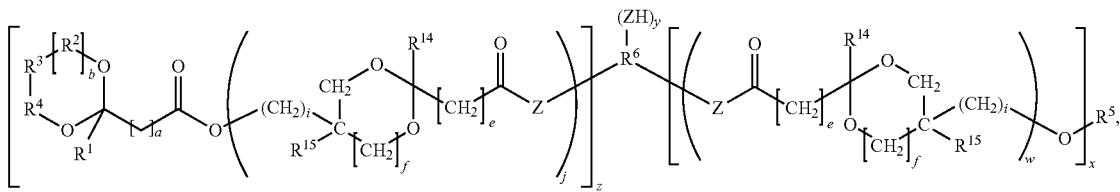

(II)

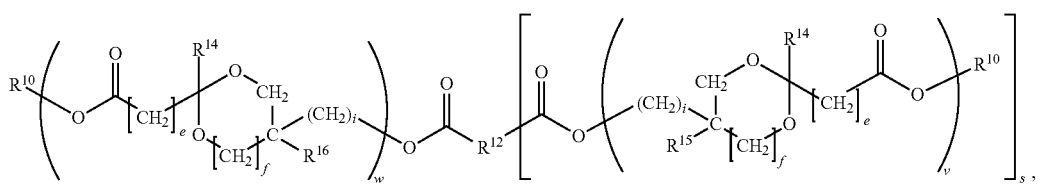

(III)

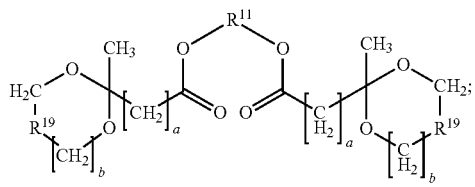

or
combinations thereof, wherein
each a, independently, is from 0 or an integer of 1 to 12;
each b, independently, is 0 or 1;
c is from 0 to 12;
d is 0 or 1;
each e, independently, is from 0 to 12;
each f, independently, is from 0 to 12;
each i is 0 or 1;
each j, independently, is 0 to 100;
each $R^1$, independently, is a hydrogen, a hydrocarbyl group, or a substituted hydrocarbyl group;
each $R^2$, $R^3$ and $R^4$ are independently methylene, alkylmethylene, or dialkylmethylene;
$R^5$ is a hydrogen or

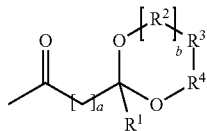

$R^6$ is a hydrocarbyl group or a substituted hydrocarbyl group;
each $R^7$, independently, is a hydrogen, a hydrocarbyl or a substituted hydrocarbyl group;
each $R^8$, independently, is a hydrogen, a hydrocarbyl or a substituted hydrocarbyl group;
each $R^{10}$, independently, is a hydrocarbyl or a substituted hydrocarbyl group;
$R^{11}$ is a hydrocarbyl, a substituted hydrocarbyl, or a hydrocarbyl group terminated with one or more heteroatoms to form a cyclic membered ring and which can include one or more of —O—, —NH—, —NR—, wherein R is a hydrocarbyl or a substituted hydrocarbyl;
$R^{12}$, is a covalent bond, a hydrocarbyl group or a substituted hydrocarbyl group;
each $R^{14}$, independently, is a hydrogen, a hydrocarbyl, or a substituted hydrocarbyl group;
each $R^{15}$, independently, is a hydrogen, a hydrocarbyl, or a substituted hydrocarbyl group;
each $R^{19}$, independently, is a hydrocarbyl, a substituted hydrocarbyl, or a hydrocarbyl group substituted with up to 5 hydroxyl groups;
each $R^{23}$ is a hydrocarbyl group or substituted hydrocarbyl group having between 1 and 12 carbon atoms
each Z, independently, is —O—, —NH— or —NR— where R is a hydrocarbyl or a substituted hydrocarbyl group;
n is from 1 to 100;
s is at least one;
v is from 0 to 100;
w is from 1 to 100;
x is at least 1;
y is 0 or a positive number.

59. The process of paragraph 58, wherein the plasticizer is the compound of formula (I) wherein b is 0, i is 1, $R^1$ is a hydrocarbyl, $R^3$ is an alkylmethylene, $R^4$ is a methylene, $R^7$ is a H, $R^8$ is a hydrocarbyl group, $R^{23}$ is a hydrocarbyl group, c is 2, d is 0 and n=1.

60. The process of paragraph 59, wherein b is 0, i is 1, $R^1$ is a methyl group, $R^3$ is $CH_3CH$, $R^4$ is a methylene, $R^7$ is a H, $R^8$ is a methyl group, $R^{23}$ is an ethyl group, c is 2, d is 0 and n=1.

61. The process of paragraph 58, wherein the plasticizer is the compound of formula (IV) wherein $R^{11}$ is a C4 alkyl.

62. The process of paragraph 61, wherein each a=2 and each b=0.

63. The process of any of paragraphs 57 through 62, wherein the antioxidant is a hindered phenol with an ester group, a hindered phenol diamide, a hindered phenol with an ether-ester linkage, a hindered phenol with a hydrocarbyl ester linkage, a hindered phenol, a hindered amine, a phosphite, an alpha-beta unsaturated ketone, or mixtures thereof.

64. The composition of paragraph 63, wherein the antioxidant is a hindered phenol.

65. The composition of paragraph 63, comprising the antioxidant which is a hindered phenol with an ester group.

66. The process of any of paragraphs 57 through 65, further comprising adding a UV stabilizer after the contacting step.

67. The process of paragraph 66, wherein the UV stabilizer is a 2-hydroxyphenyl-benzophenone, a 2-(2-hydroxypeyl)-benzotriazole, a 2-hydroxyphenyl-s-triazine), or mixtures thereof.

68. The composition of paragraph 67, wherein the UV stabilizer is ethanediamide, N-(2-ethoxyphenyl)-N'-(2-ethylphenyl)-.

69. The process of any of paragraphs 57 through 68, wherein the thermal stabilizer is a Group I or Group II metal stearate.

70. The process of paragraph 69, wherein the thermal stabilizer is sodium or calcium stearate.

71. The process of any of paragraphs 57 through 72, wherein the catalyst is a metal alkoxide.

72. The process of paragraph 71, wherein the metal ion is titanium.

73. The process of paragraph 71, wherein the metal alkoxide is titanium isopropoxide.

74. The process of any of claims 57 through 73, wherein the process is conducted at a temperature range of from about 150° C. to about 250° C.

75. The process of any of paragraphs 57 through 74, wherein the plasticizer has a color index (YI) of less than 50 measured by ASTM method E313.

76. The process of any of paragraphs 57 through 74, wherein the plasticizer has a color index (YI) of less than 20 measured by ASTM method E313.

77. The process of any of paragraphs 57 through 74, wherein the plasticizer has a color index (YI) of less than 5 measured by ASTM method E313.

78. The process of any of paragraphs 57 through 74, wherein the plasticizer has a color index (YI) of less than 1 measured by ASTM method E313.

79. The process of any of paragraphs 57 through 78, wherein the mass loss of the plasticizer is less than 2% after 10 days at 110° C. and less than 15% RH.

80. A process to prepare a plasticizer, wherein the plasticizer has a molecular weight of greater than 300 with at least 2 alkyl ketal ester moieties, comprising the step: contacting under reaction conditions an alkyl ketal ester, a multihydric hydrocarbyl moiety, or a monohydric alkyl ketal ester; a catalyst; and an adsorbent, carbon, alumina, a buffer solution, a basic solution or mixtures thereof, wherein a plasticizer comprising at least 2 alkyl ketal ester moieties with a molecular weight of greater than 300 is obtained.

81. The process of paragraph 80, wherein the plasticizer has a formula comprising:

$R^5$ is a hydrogen or

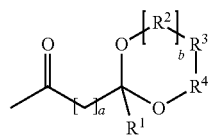

$R^6$ is a hydrocarbyl group or a substituted hydrocarbyl group;
each $R^7$, independently, is a hydrogen, a hydrocarbyl or a substituted hydrocarbyl group;
each $R^8$, independently, is a hydrogen, a hydrocarbyl or a substituted hydrocarbyl group;
each $R^{10}$, independently, is a hydrocarbyl or a substituted hydrocarbyl group;
$R^{11}$ is a hydrocarbyl, a substituted hydrocarbyl, or a hydrocarbyl group terminated with one or more heteroatoms to (I)

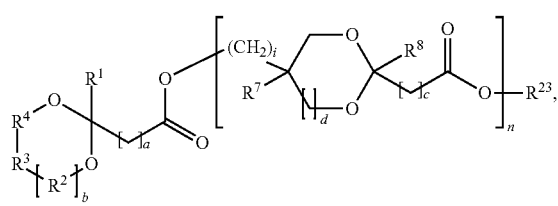

(II)

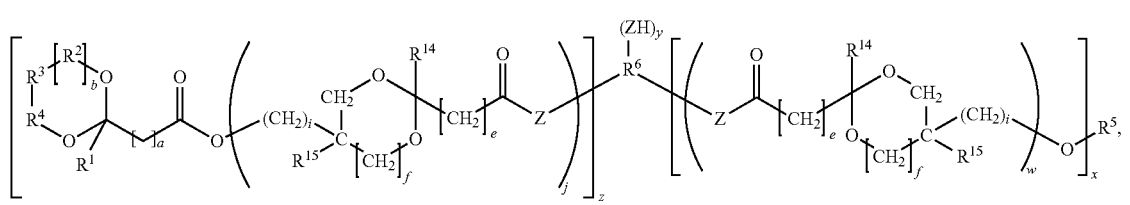

(III)

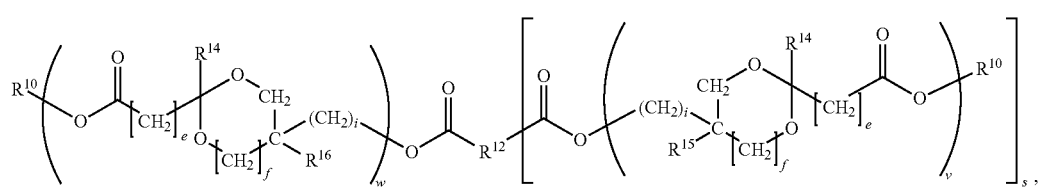

(IV)

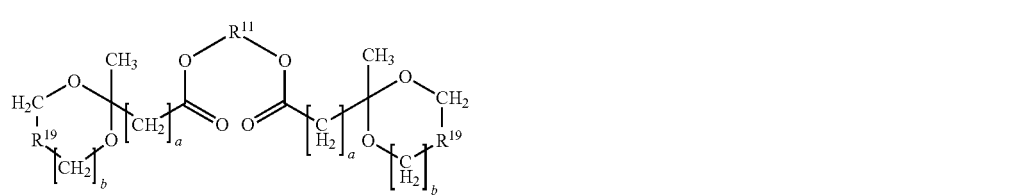

or
combinations thereof, wherein
each a, independently, is from 0 or an integer of 1 to 12;
each b, independently, is 0 or 1;
c is from 0 to 12;
d is 0 or 1;
each e, independently, is from 0 to 12;
each f, independently, is from 0 to 12;
each i is 0 or 1;
each j, independently, is 0 to 100;
each $R^1$, independently, is a hydrogen, a hydrocarbyl group, or a substituted hydrocarbyl group;
each $R^2$, $R^3$ and $R^4$ are independently methylene, alkylmethylene, or dialkylmethylene;

form a cyclic membered ring and which can include one or more of —O—, —NH—, —NR—, wherein R is a hydrocarbyl or a substituted hydrocarbyl;
$R^{12}$, is a covalent bond, a hydrocarbyl group or a substituted hydrocarbyl group;
each $R^{14}$, independently, is a hydrogen, a hydrocarbyl, or a substituted hydrocarbyl group;
each $R^{15}$, independently, is a hydrogen, a hydrocarbyl, or a substituted hydrocarbyl group;
each $R^{19}$, independently, is a hydrocarbyl, a substituted hydrocarbyl, or a hydrocarbyl group substituted with up to 5 hydroxyl groups;
each $R^{23}$ is a hydrocarbyl group or substituted hydrocarbyl group having between 1 and 12 carbon atoms each Z, independently, is —O—, —NH— or —NR— where R is a hydrocarbyl or a substituted hydrocarbyl group;
n is from 1 to 100;
s is at least one;
v is from 0 to 100;
w is from 1 to 100;
x is at least 1;
y is 0 or a positive number.

82. The process of paragraph 81, wherein the plasticizer is the compound of formula (I) wherein b is 0, i is 1, $R^1$ is a hydrocarbyl, $R^3$ is an alkylmethylene, $R^4$ is a methylene, $R^7$ is a H, $R^8$ is a hydrocarbyl group, $R^{23}$ is a hydrocarbyl group, c is 2, d is 0 and n=1.

83. The process of paragraph 82, wherein b is 0, i is 1, $R^1$ is a methyl group, $R^3$ is $CH_3CH$, $R^4$ is a methylene, $R^7$ is a H, $R^8$ is a methyl group, $R^{23}$ is an ethyl group, c is 2, d is 0 and n=1.

84. The process of paragraph 81, wherein the plasticizer is the compound of formula (IV) wherein $R^{11}$ is a C4 alkyl.

85. The process of paragraph 84, wherein each a=2 and each b=0.

86. The process of any of paragraphs 80 through 85, further comprising a step of adding an antioxidant, or a thermal stabilizer during the reaction conditions.

87. The process of paragraph 86, wherein the antioxidant is a hindered phenol with an ester group, a hindered phenol diamide, a hindered phenol with an ether-ester linkage, a hindered phenol with a hydrocarbyl ester linkage, a hindered phenol, a hindered amine, a phosphite, an alpha-beta unsaturated ketone, or mixtures thereof 88. The process of paragraph 87, wherein the antioxidant is a hindered phenol.

89. The process of paragraph 87, wherein the antioxidant is a hindered phenol with an ester group.

90. The process of paragraph 86, wherein the thermal stabilizer is a Group I or Group II metal stearate.

91. The composition of paragraph 90, wherein the thermal stabilizer is sodium or calcium stearate.

92. The process of any of paragraphs 80 through 91, wherein the catalyst is a metal alkoxide.

93. The process of paragraph 92, wherein the metal ion is titanium.

94. The process of paragraph 92, wherein the metal alkoxide is titanium isopropoxide.

95. The process of any of claims 80 through 94, wherein the process is conducted at a temperature range of from about 150° C. to about 250° C.

96. The process of any of paragraphs 80 through 95, wherein the plasticizer has a color index (YI) of less than 50 measured by ASTM method E313.

97. The process of any of paragraphs 80 through 95, wherein the plasticizer has a color index (YI) of less than 20 measured by ASTM method E313.

98. The process of any of paragraphs 80 through 95, wherein the plasticizer has a color index (YI) of less than 5 measured by ASTM method E313.

99. The process of any of paragraphs 80 through 95, wherein the plasticizer has a color index (YI) of less than 1 measured by ASTM method E313.

100. The process of any of paragraphs 80 through 99, wherein the mass loss of the plasticizer is less than 2% after 10 days at 110° C. and less than 15% RH.

101. The process of any of paragraphs 80 through 100, wherein the adsorbent is calcium oxide.

102. A process to prepare a plasticizer, wherein the plasticizer comprises at least 2 alkyl ketal ester moieties with a molecular weight of greater than 300, comprising the step: contacting an alkyl ketal ester, a multihydric hydrocarbyl moiety, or a monohydric alkyl ketal ester; a catalyst; and optionally, an antioxidant under reaction conditions, wherein the reaction is conducted without the substantial presence of air, providing a plasticizer that has a color index (YI) of less than 50 measured by ASTM method E313 having at least 2 alkyl ketal ester moieties with a molecular weight of greater than 300.

103. The process of paragraph 102, wherein the plasticizer has a color index (YI) of less than 20 measured by ASTM method E313.

104. The process of any of paragraph 102, wherein the plasticizer has a color index (YI) of less than 5 measured by ASTM method E313.

105. The process of paragraph 102, wherein the plasticizer has a color index (YI) of less than 1 measured by ASTM method E313.

106. The process of any of paragraphs 102 through 105, wherein the plasticizer has a purity of at least 90%.

107. The process of any of paragraphs 102 through 106, wherein the plasticizer has a formula comprising:

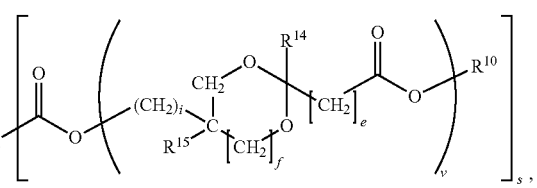

(III)

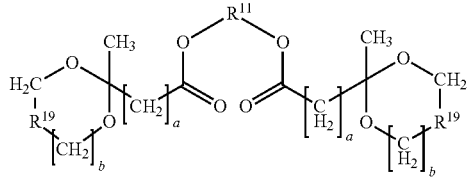

(IV)

or combinations thereof, wherein
each a, independently, is from 0 or an integer of 1 to 12;
each b, independently, is 0 or 1;
c is from 0 to 12;
d is 0 or 1;
each e, independently, is from 0 to 12;
each f, independently, is from 0 to 12;
each i is 0 or 1;
each j, independently, is 0 to 100;
each $R^1$, independently, is a hydrogen, a hydrocarbyl group, or a substituted hydrocarbyl group;
each $R^2$, $R^3$ and $R^4$ are independently methylene, alkylmethylene, or dialkylmethylene;
$R^5$ is a hydrogen or

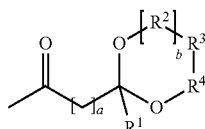

$R^6$ is a hydrocarbyl group or a substituted hydrocarbyl group;
each $R^7$, independently, is a hydrogen, a hydrocarbyl or a substituted hydrocarbyl group;
each $R^8$, independently, is a hydrogen, a hydrocarbyl or a substituted hydrocarbyl group;
each $R^{10}$, independently, is a hydrocarbyl or a substituted hydrocarbyl group;
$R^{11}$ is a hydrocarbyl, a substituted hydrocarbyl, or a hydrocarbyl group terminated with one or more heteroatoms to form a cyclic membered ring and which can include one or more of —O—, —NH—, —NR—, wherein R is a hydrocarbyl or a substituted hydrocarbyl;
$R^{12}$, is a covalent bond, a hydrocarbyl group or a substituted hydrocarbyl group;
each $R^{14}$, independently, is a hydrogen, a hydrocarbyl, or a substituted hydrocarbyl group;
each $R^{15}$, independently, is a hydrogen, a hydrocarbyl, or a substituted hydrocarbyl group;
each $R^{19}$, independently, is a hydrocarbyl, a substituted hydrocarbyl, or a hydrocarbyl group substituted with up to 5 hydroxyl groups;
each $R^{23}$ is a hydrocarbyl group or substituted hydrocarbyl group having between 1 and 12 carbon atoms each Z, independently, is —O—, —NH— or —NR— where R is a hydrocarbyl or a substituted hydrocarbyl group;
n is from 1 to 100;
s is at least one;
v is from 0 to 100;
w is from 1 to 100;
x is at least 1;
y is 0 or a positive number.

108. The process of paragraph 107, wherein the plasticizer is the compound of formula (I) wherein b is 0, i is 1, $R^1$ is a hydrocarbyl, $R^3$ is an alkylmethylene, $R^4$ is a methylene, $R^7$ is a H, $R^8$ is a hydrocarbyl group, $R^{23}$ is a hydrocarbyl group, c is 2, d is 0 and n=1.

109. The process of paragraph 108, wherein b is 0, i is 1, $R^1$ is a methyl group, $R^3$ is $CH_3CH$, $R^4$ is a methylene, $R^7$ is a H, $R^8$ is a methyl group, $R^{23}$ is an ethyl group, c is 2, d is 0 and n=1.

110. The process of paragraph 107, wherein the plasticizer is the compound of formula (IV) wherein $R^{11}$ is a C4 alkyl.

111. The process of paragraph 110, wherein each a=2 and each b=0.

112. The process of any of paragraphs 102 through 111, further comprising a step of adding an antioxidant, a UV stabilizer or a thermal stabilizer during the reaction conditions.

113. The process of paragraph 112, wherein the antioxidant is a hindered phenol with an ester group, a hindered phenol diamide, a hindered phenol with an ether-ester linkage, a hindered phenol with a hydrocarbyl ester linkage, a hindered phenol, a hindered amine, a phosphite, an alpha-beta unsaturated ketone, or mixtures thereof.

114. The composition of paragraph 113, wherein the antioxidant is a hindered phenol.

115. The composition of paragraph 113, wherein the antioxidant is a hindered phenol with an ester group.

116. The process of paragraph 102 further comprising, adding a UV stabilizer after the contacting step.

117. The process of paragraph 116, wherein the UV stabilizer is a 2-hydroxyphenyl-benzophenone, a 2-(2-hydroxypeyl)-benzotriazole, a 2-hydroxyphenyl-s-triazine), or mixtures thereof.

118. The composition of paragraph 116, wherein the UV stabilizer is ethanediamide, N-(2-ethoxyphenyl)-N'-(2-ethylphenyl)-.

119. The process of paragraph 112, wherein the thermal stabilizer is a Group I or Group II metal stearate.

120. The process of any of paragraphs 102 through 119, wherein the catalyst is a metal alkoxide.

121. The process of paragraph 120, wherein the metal ion is titanium.

122. The process of paragraph 120, wherein the metal alkoxide is titanium isopropoxide.

123. The process of any of claims 102 through 122, wherein the process is conducted at a temperature range of from about 150° C. to about 250° C.

124. The process of any of paragraphs 102 through 123, wherein the plasticizer has a color index (YI) of less than 40 measured by ASTM method E313.

125. The process of any of paragraphs 102 through 124, wherein the plasticizer has a color index (YI) of less than 20 measured by ASTM method E313.

126. The process of any of paragraphs 102 through 124, wherein the plasticizer has a color index (YI) of less than 5 measured by ASTM method E313.

127. The process of any of paragraphs 102 through 124, wherein the plasticizer has a color index (YI) of less than 1 measured by ASTM method E313.

128. The process of any of paragraphs 102 through 127, wherein the mass loss of the plasticizer is less than 2% after 10 days at 110° C. and less than 15% RH.

129. The process of any of paragraphs 102 through 128, wherein the adsorbent is calcium oxide.

130. The process of any of paragraphs 102 through 129, wherein the ppm of oxygen present in the reaction mixture is less than about 1000 ppm.

131. A process to prepare a plasticizer, wherein the plasticizer comprises at least 2 alkyl ketal ester moieties with a molecular weight of greater than 300, comprising the step: contacting the plasticizer with a molecular weight of greater than 300 and at least 2 alkyl ketal ester moieties with hydrogen under hydrogenation conditions, providing a purified plasticizer that has a color index (YI) of less than 50 measured by ASTM method E313 having at least 2 alkyl ketal ester moieties with a molecular weight of greater than 300.

132. The process of paragraph 131, wherein the purified plasticizer has a purity of at least 90%.

133. The process of paragraphs 131 or 132, wherein the plasticizer has a formula comprising:

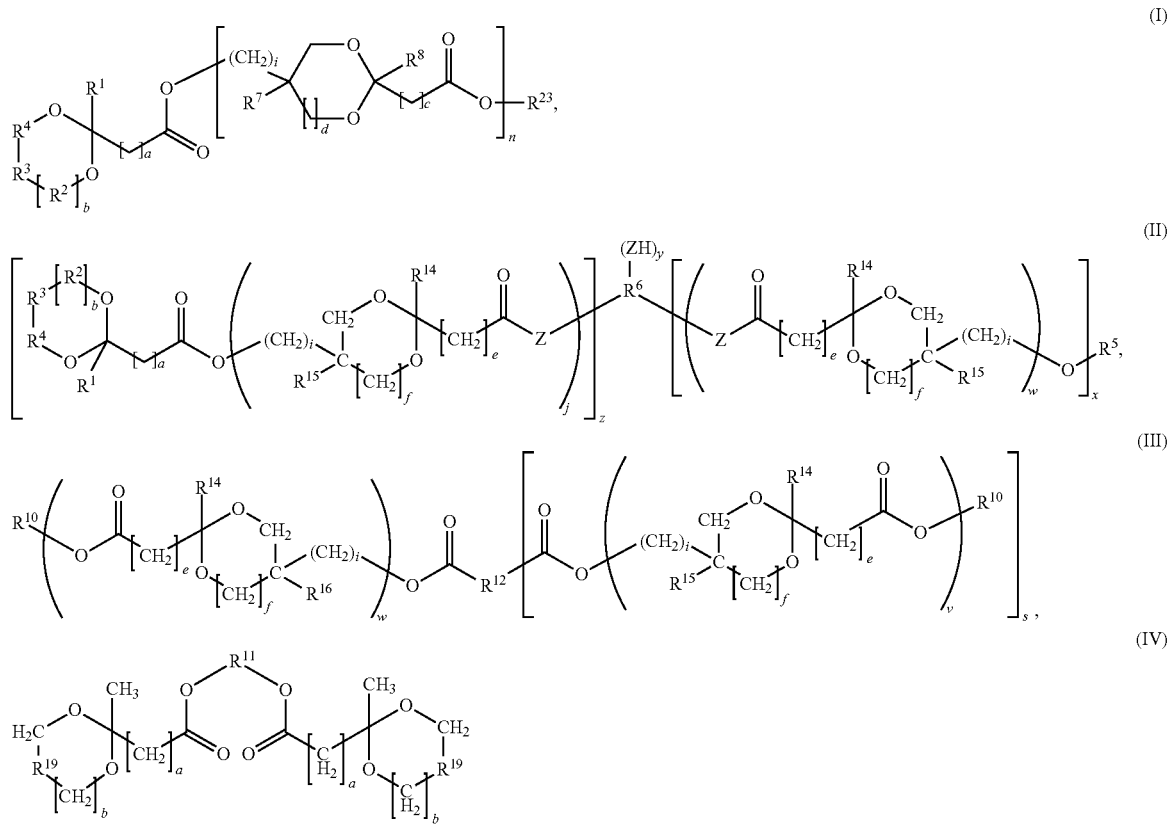

or combinations thereof, wherein each a, independently, is from 0 or an integer of 1 to 12;

each b, independently, is 0 or 1;

c is from 0 to 12;

d is 0 or 1;

each e, independently, is from 0 to 12;

each f, independently, is from 0 to 12;

each i is 0 or 1;

each j, independently, is 0 to 100;

each $R^1$, independently, is a hydrogen, a hydrocarbyl group, or a substituted hydrocarbyl group;

each $R^2$, $R^3$ and $R^4$ are independently methylene, alkylmethylene, or dialkylmethylene;

$R^5$ is a hydrogen or

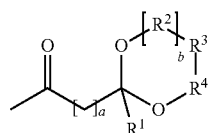

R⁶ is a hydrocarbyl group or a substituted hydrocarbyl group;

each R⁷, independently, is a hydrogen, a hydrocarbyl or a substituted hydrocarbyl group;

each R⁸, independently, is a hydrogen, a hydrocarbyl or a substituted hydrocarbyl group;

each R¹⁰, independently, is a hydrocarbyl or a substituted hydrocarbyl group;

R¹¹ is a hydrocarbyl, a substituted hydrocarbyl, or a hydrocarbyl group terminated with one or more heteroatoms to form a cyclic membered ring and which can include one or more of —O—, —NH—, —NR—, wherein R is a hydrocarbyl or a substituted hydrocarbyl;

R¹², is a covalent bond, a hydrocarbyl group or a substituted hydrocarbyl group;

each R¹⁴, independently, is a hydrogen, a hydrocarbyl, or a substituted hydrocarbyl group;

each R¹⁵, independently, is a hydrogen, a hydrocarbyl, or a substituted hydrocarbyl group;

each R¹⁹, independently, is a hydrocarbyl, a substituted hydrocarbyl, or a hydrocarbyl group substituted with up to 5 hydroxyl groups;

each R²³ is a hydrocarbyl group or substituted hydrocarbyl group having between 1 and 12 carbon atoms each Z, independently, is —O—, —NH— or —NR— where R is a hydrocarbyl or a substituted hydrocarbyl group;

n is from 1 to 100;
s is at least one;
v is from 0 to 100;
w is from 1 to 100;
x is at least 1;
y is 0 or a positive number.

134. The process of paragraph 133, wherein the plasticizer is the compound of formula (I) wherein b is 0, i is 1, R¹ is a hydrocarbyl, R³ is an alkylmethylene, R⁴ is a methylene, R⁷ is a H, R⁸ is a hydrocarbyl group, R²³ is a hydrocarbyl group, c is 2, d is 0 and n=1.

135. The process of paragraph 134, wherein b is 0, i is 1, R¹ is a methyl group, R³ is CH₃CH, R⁴ is a methylene, R⁷ is a H, R⁸ is a methyl group, R²³ is an ethyl group, c is 2, d is 0 and n=1.

136. The process of paragraph 133, wherein the plasticizer is the compound of formula (IV) wherein R¹¹ is a C4 alkyl.

137. The process of paragraph 136, wherein each a=2 and each b=0.

138. The process of any of paragraphs 131 through 137, further comprising a step of adding an antioxidant, a UV stabilizer or a thermal stabilizer during the reaction conditions.

139. The process of paragraph 138, wherein the antioxidant is a hindered phenol with an ester group, a hindered phenol diamide, a hindered phenol with an ether-ester linkage, a hindered phenol with a hydrocarbyl ester linkage, a hindered phenol, a hindered amine, a phosphite, an alpha-beta unsaturated ketone, or mixtures thereof.

140. The process of paragraph 139, wherein the antioxidant is a hindered phenol.

141. The process of paragraph 139, comprising the antioxidant which is a hindered phenol with an ester group.

142. The process of paragraphs 131 through 141 further comprising, adding a UV stabilizer after the contacting step.

143. The process of paragraph 142 wherein the UV stabilizer is a 2-hydroxyphenyl-benzophenone, a 2-(2-hydroxypeyl)-benzotriazole, a 2-hydroxyphenyl-s-triazine), or mixtures thereof.

144. The process of paragraph 143, wherein the UV stabilizer is ethanediamide, N-(2-ethoxyphenyl)-N'-(2-ethylphenyl)-.

145. The process of paragraph 138, wherein the thermal stabilizer is a Group I or Group II metal stearate.

146. The process of paragraph 145, wherein the thermal stabilizer is sodium or calcium stearate.

147. The process of any of paragraphs 131 through 146, wherein the catalyst is a metal alkoxide.

148. The process of paragraph 147, wherein the metal ion is titanium.

149. The process of paragraph 147, wherein the metal alkoxide is titanium isopropoxide.

150. The process of any of claims 131 through 149, wherein the process is conducted at a temperature range of from about 150° C. to about 250° C.

151. The process of any of paragraphs 131 through 149, wherein the plasticizer has a color index (YI) of less than 50 measured by ASTM method E313.

152. The process of any of paragraphs 131 through 149, wherein the plasticizer has a color index (YI) of less than 20 measured by ASTM method E313.

153. The process of any of paragraphs 131 through 149, wherein the plasticizer has a color index (YI) of less than 5 measured by ASTM method E313.

154. The process of any of paragraphs 131 through 149, wherein the plasticizer has a color index (YI) of less than 1 measured by ASTM method E313.

155. The process of any of paragraphs 131 through 154, wherein the mass loss of the plasticizer is less than 2% after 10 days at 110° C. and less than 15% RH.

156. The process of any of paragraphs 131 through 155 wherein the adsorbent is calcium oxide.

157. The process of any of paragraphs 131 through 156, wherein the reaction is performed under increased pressure.

158. The process of paragraph 157, wherein the hydrogen pressure is at least 100 psi.

159. A plasticizer made by the method of paragraphs 131-158.

160. The process of paragraph 119, wherein the thermal stabilizer is sodium or calcium stearate.

161. The process of any of paragraphs 80 through 101, further comprising adding a UV stabilizer after the contacting step.

162. The process of paragraph 161, wherein the UV stabilizer is a 2-hydroxyphenyl-benzophenone, a 2-(2-hydroxypeyl)-benzotriazole, a 2-hydroxyphenyl-s-triazine), or mixtures thereof.

163. The process of paragraph 161, wherein the UV stabilizer is ethanediamide, N-(2-ethoxyphenyl)-N'-(2-ethylphenyl)-.

The invention will be further described with reference to the following non-limiting Examples. It will be apparent to those skilled in the art that many changes can be made in the embodiments described without departing from the scope of the present invention. Thus the scope of the present invention should not be limited to the embodiments described in this application, but only by embodiments described by the language of the claims and the equivalents of those embodiments. Unless otherwise indicated, all percentages are by weight.

EXAMPLES

Formulae for Examples for the following section

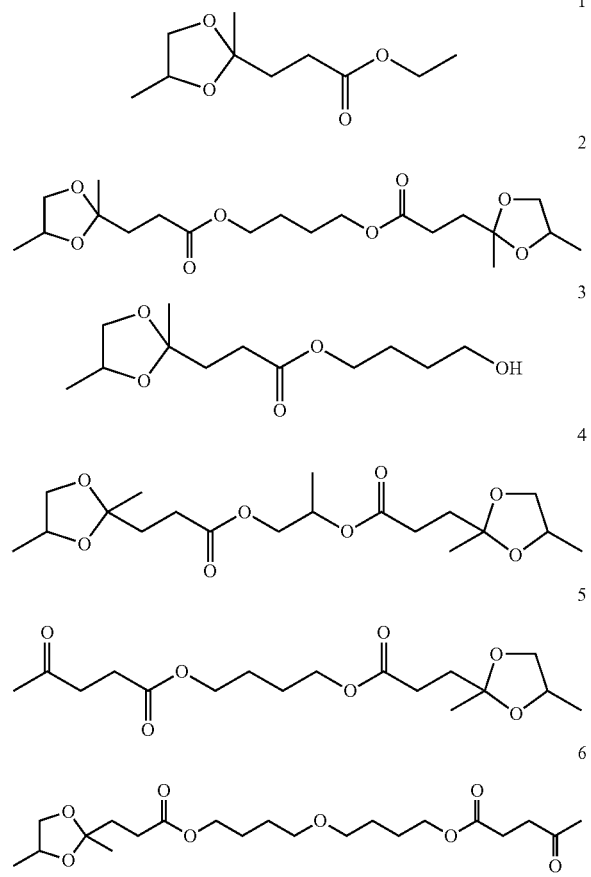

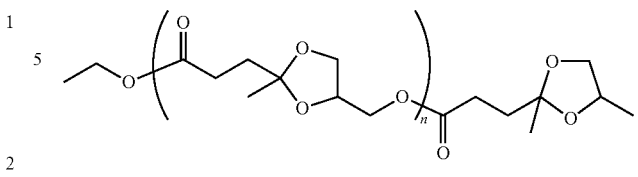

Example 1. 1,4 Butanediol (22.5 g, 0.25 mol) and 1 (151.7 g, 0.75 mol) was added to an empty 250 mL, 3-neck round bottom flask equipped with a magnetic stir-bar, Dean-Stark trap and overhead condenser, a thermocouple, and a glass stopper. The contents were dried by heating with a heating mantle overnight at 85° C. under 15 Torr vacuum. The flask was back-filled with nitrogen, a sample was taken from the flask, and the water content in the flask was measured to be less than 15 ppm using Karl Fischer analysis. Then (6.8 µL, 11 ppm Ti) of titanium tetra-isoproxide was added into the flask. A nitrogen purge was maintained during the course of the reaction and the contents of the flask were heated to 185° C. using a heating mantle. During the reaction, liquid was observed to collect in the Dean-Stark trap. After 3 hours from the time volatiles started to come over, the reaction mixture was allowed to cool to ambient temperature. A sample was taken from the flask and analyzed by GC-FID and GPC. The composition was measured by GC-FID and found to be: 65.3% of 2, 0.50% of 3, 33.6% of 1, and 0.2% higher molecular weight species.

Excess 1 was removed by vacuum distillation. The composition of the final product after distillation was measured by GC-FID and found to be: 94.7% of 2, 0.60% of 3, 3.6% of 1, and 0.3% higher molecular weight species.

Examples 2-4 were synthesized under the same conditions as Example 1 with different ratios of 1:1,4-butanediol (BDO). The equivalents of 1 and the final reaction compositions are shown in Table 1. Distillation data is given in Table 2.

TABLE 1

Reaction composition data for Examples 1-4.

| Example | 1:BDO Ratio | 2 (GC-FID Area %) | 3 (GC-FID Area %) | 1 (GC-FID Area %) | 4 (GC-FID Area %) | 5 (GC-FID Area %) | 6 (GC-FID Area %) | Higher MW (GC-FID Area %) | Higher MW (GPC Area %) | YI E313 [C/2] |
|---|---|---|---|---|---|---|---|---|---|---|
| 1 | 3.0 | 65.3 | 0.5 | 33.6 | 0.05 | 0.22 | 0.02 | 0.0 | 0.0 | 12.5 |
| 2 | 2.8 | 68.1 | 1.3 | 29.0 | 0.49 | 0.22 | 0.25 | 0.1 | 0.3 | 17.6 |
| 3 | 2.6 | 74.9 | 1.2 | 22.9 | 0.17 | 0.29 | 0.05 | 0.04 | 0.0 | 19.7 |
| 4 | 2.5 | 70.6 | 5.0 | 23.1 | 0.19 | 0.32 | 0.15 | 0.05 | 0.0 | 8.6 |

The data shows that varying the ratio of 1 to BDO produces a high yield of 2 in relation to the side products, 4-6. Typical compositions of the product composition are shown in Table 2.

TABLE 2

Product Composition of Examples 1 and 3 after vacuum distillation.

| Example | 2 (GC-FID Area %) | 3 (GC-FID Area %) | 1 (GC-FID Area %) | 4 (GC-FID Area %) | 5 (GC-FID Area %) | 6 (GC-FID Area %) | Higher MW (GC-FID Area %) | Higher MW (GPC Area %) | YI E313 [C/2] |
|---|---|---|---|---|---|---|---|---|---|
| 1 | 94.7 | 0.6 | 3.6 | 0.10 | 0.31 | 0.02 | 0.3 | 0.0 | 35.3 |
| 3 | 93.8 | 1.3 | 3.7 | 0.53 | 0.01 | 0.06 | 0.3 | 0.0 | 33.9 |

Example 5. 1,4 Butanediol (16.21 g, 0.18 mol) and 1 (108.89 g, 0.54 mol) were added to an empty 250 mL, 3-neck round bottom flask equipped with a magnetic stir-bar, a thermocouple, a glass stopper, and a vacuum adapter from which vacuum and nitrogen could be applied. The contents were dried by heating with a heating mantle overnight at 60° C.under 5-10 Torr vacuum. The flask was back-filled with nitrogen, a sample was taken from the flask, and the water content in the flask was measured to be less than 35 ppm water using Karl Fischer analysis. The glass stopper was removed from the round bottom flask and was replaced with a Dean stark, condenser and an outlet to a bubbler. Then (4.9 μL, 11 ppmTi) of titanium tetra-isoproxide was added into the flask. A nitrogen purge was maintained during the course of the reaction and the contents of the flask were heated to 180° C. using a heating mantle. During the reaction, liquid was observed to collect in the Dean-Stark trap. After 3 hours from the time volatiles started to come over, the reaction mixture was allowed to cool to ambient temperature.

A sample was taken from the flask and analyzed by GC-FID. The color of the reaction mixture was also measured using a colorimeter. The composition was measured by GC-FID and it is displayed in Table 3 (Example 5a).

Excess 1 was removed by vacuum distillation. The composition of the final product was measured by GC-FID and it is displayed in Table 4 (Example 5b).

Example 6a-6b was synthesized and purified under the same conditions as Example 5a-5b.

Examples 7-13 were synthesized and purified under the same conditions as Examples 6a-6b. Example 7 contained 120 ppm Irgafos® 168 and Irganox® 1010, Example 8 used 1, which had been re-purified by 3 additional fractional distillations before use, and 120 ppm each of Irgafos® 168 and Irganox® 1010, Example 9 used 30 ppm each of Irgafos 168® and Irganox 1010®, and Example 10 used 2000 ppm each of Irgafos 168® and Irganox® 1010. Example 11 used 2000 ppm of Irganox® 1010. Example 12 was synthesized according to Example 7. Example 13 was synthesized according to Example 7, however, 1 was re-purified by an additional fractional distillation before use. The final reaction compositions for Examples 5-6 are shown in Table 3 (Examples 5a-6a). Final product composition after purification is given in Table 4 (Examples 5b-6b). The antioxidants were added into the reactor along with the reactants prior to the drying step at 60° C.

TABLE 3

Reaction composition data for Examples 5 and 6.

| Example | 2 (GC-FID Area %) | 3 (GC-FID Area %) | 1 (GC-FID Area %) | 4 (GC-FID Area %) | 5 (GC-FID Area %) | 6 (GC-FID Area %) | Oligomers (GC-FID Area %) | % Selectivity [2/(2 + 4 + 5 + 6 + oligomers)] | YI E313 [c/10] |
|---|---|---|---|---|---|---|---|---|---|
| 5a | 64.95 | 0.38 | 33.71 | 0.10 | 0.34 | 0.04 | 0.05 | 99 | 9.12 |
| 6a | 65.20 | 0.40 | 33.35 | 0.11 | 0.38 | 0.06 | 0.11 | 99 | 10.86 |

TABLE 4

Composition of Examples 5-10 after vacuum distillation.

| Example | 2 (GC-FID Area %) | 3 (GC-FID Area %) | 1 (GC-FID Area %) | 4 (GC-FID Area %) | 5 (GC-FID Area %) | 6 (GC-FID Area %) | Oligomers (GC-FID Area %) | % Selectivity [2/(2 + 4 + 5 + 6 + oligomers)] | YI E313 [c/10] |
|---|---|---|---|---|---|---|---|---|---|
| 5b | 98.28 | 0.32 | 0.08 | 0.16 | 0.52 | 0.07 | 0.19 | 99 | 33.69 |
| 6b | 97.70 | 0.40 | 0.51 | 0.15 | 0.55 | 0.08 | 0.18 | 99 | 20.48 |
| 7 | 97.60 | 0.47 | 0.60 | 0.13 | 0.45 | 0.07 | 0.25 | 99 | 13.59 |
| 8 | 98.83 | 0.25 | 0.05 | 0.06 | 0.20 | 0.02 | 0.16 | 99 | 11.39 |
| 9 | 98.69 | 0.17 | 0.03 | 0.12 | 0.46 | 0.06 | 0.20 | 99 | 18.98 |
| 10 | 94.43 | 3.26 | 0.03 | 0.04 | 0.44 | 0.05 | 1.46 | 98 | 8.76 |
| 11 | 98.18 | 0.17 | 0.02 | 0.03 | 0.40 | 0.05 | 0.93 | 99 | 11.96 |
| 12 | 98.40 | 0.36 | 0.02 | 0.11 | 0.48 | 0.03 | 0.19 | 99 | 9.85 |
| 13 | 98.93 | 0.14 | 0.03 | 0.08 | 0.24 | 0.06 | 0.19 | 99 | 11.24 |

The data in the table showed that Examples. 7-13 show a significant improvement in color (YI) compared to Examples. 5-6, due to the addition of anti-oxidants prior to the condensation reaction. Additionally, Example 11 (0 ppm Irgafos® 168) shows an improvement in final product composition compared to Example 10 due to the absence of a higher level of phosphite secondary antioxidant (2000 ppm Irgafos® 168 in Example 10).

Example 14. 1,4 Butanediol (16.21 g, 0.18 mol) and 1 (108.89 g, 0.54 mol) was added to an empty 250 mL, 3-neck round bottom flask equipped with a magnetic stir-bar, a thermocouple, a vacuum adapter from which vacuum and nitrogen could be applied, a dean-stark, a condenser and an outlet to a bubbler. Then (4.9 µL, 11 ppmTi) of titanium tetra-isoproxide was added into the flask. With the reaction mixture at ambient temperature the vacuum was applied in order to degas the system. Once degassing was complete, a nitrogen purge was maintained during the course of the reaction and the contents of the flask were heated to 180° C. using a heating mantle. During the reaction, liquid was observed to collect in the Dean-Stark trap. After 3 hours from the time volatiles started to come over, the reaction mixture was allowed to cool to ambient temperature.

Example 15 was synthesized under the same conditions as Example 14. The total reaction time was 9 hours 10 minutes (Example 15b). A sample was withdrawn during the reaction to determine the reaction conversion after 3 h (Example 15a). The reaction compositions are shown in Table 5.

Examples 16-17 were synthesized under the same conditions as Example 15.

TABLE 5

Reaction composition data for Examples 14-17.

| Example | Initial Acid Number of 1 | 2 (GC-FID Area %) | 3 (GC-FID Area %) | 1 (GC-FID Area %) | 4 (GC-FID Area %) | 5 (GC-FID Area %) | 6 (GC-FID Area %) | Oligomers (GC-FID Area %) | % Selectivity [2/(2 + 4 + 5 + 6 + oligomers)] | YI (ASTM E313) [c/10] |
|---|---|---|---|---|---|---|---|---|---|---|
| 14  | 0.07 | 64.96 | 0.36  | 33.29 | 0.17 | 0.49 | 0.06 | 0.10 | 99 | 6.72 |
| 15b | 0.11 | 55.81 | 0.26  | 30.59 | 4.14 | 4.39 | 0.85 | 1.63 | 84 | 5.26 |
| 15a | 0.11 | 37.36 | 9.05  | 42.76 | 1.18 | 2.45 | 1.37 | 0.41 | 87 |      |
| 16  | 0.26 | 40.75 | 6.59  | 39.87 | 1.38 | 2.68 | 2.00 | 0.79 | 86 | 18.35 |
| 17  | 0.87 | 21.95 | 10.33 | 45.59 | 0.64 | 7.04 | 1.12 | 0.79 | 70 | 16.97 |

The data in Table 5 shows that the acid number of the starting reagent, 1, affects the selectivity of the reaction components to combine to make 2. When 1 has an acid number <0.1, the selectivity is approximately 99%. Increasing the acid number, shows a lower selectivity toward the production of 2, and higher amounts of the undesirable side products 4-6. Example 14 was prepared from 1,4-BDO and 1, in which 1 was prepared using camphor-sulfonic acid catalyst, and subsequently buffered with dibasic sodium phosphate, then fractionally distilled. Examples 15a-15b were prepared from 1,4-BDO and 1, in which 1 was prepared from sulfuric acid catalyst, and 1 was distilled twice by fractional distillation. Examples 16-17 were prepared from 1,4-BDO and 1, in which 1 was prepared from sulfuric acid catalyst, and 1 was fractionally distilled. It is also noteworthy, that the ketalization catalyst, sulfuric acid, seemed to have an effect on the selectivity. Without being bound by theory, it is possible that certain catalysts, like sulfuric acid, or aromatic sulfonic acid catalysts, may produce ketals which display acid numbers >0.0 and lead to lead to lower selectivity of intended downstream condensation products. However, by using aliphatic sulfonic acids and/or acid-scavenging buffers during the ketal process, the selectivity of the downstream condensation product is much improved.

The thermal stability of some of the Examples listed above was tested at elevated temperatures. Each sample was placed into a tared glass vial and the weight of the sample was recorded. The glass vials were placed into an oven that was set to maintain a temperature of 115° C. at a relative humidity (RH) or 15% or less. The samples were removed from the oven on the third, seventh, and tenth day to calculate the mass loss due to degradation. The samples were allowed to cool down to ambient temperature before the weight was measured. The thermal stability data is shown in Table 6.

TABLE 6

Thermal Stability data for Examples 5-13

| Example | % Mass Loss Day 3 | % Mass Loss Day 7 | % Mass Loss Day 10 | %5 Initial (GC-FID) | %5 after Day 10 (GC-FID) |
|---|---|---|---|---|---|
| 5  | 0.91 | 2.29 | 3.36 | 0.52 | 13.8 |
| 7  | 0.71 | 1.06 | 1.70 | 0.45 | 4.4 |
| 8  | 0.14 | 0.64 | 1.51 | 0.20 | 6.4 |
| 9  | 0.26 | 1.30 | 2.20 | 0.46 | 10.0 |
| 10 | 0.24 | 0.50 | 0.68 | 0.44 | 0.5 |
| 11 | 0.11 | 0.25 | 0.32 | 0.40 | 0.5 |

TABLE 6-continued

Thermal Stability data for Examples 5-13

| Example | % Mass Loss Day 3 | % Mass Loss Day 7 | % Mass Loss Day 10 | %5 Initial (GC-FID) | %5 after Day 10 (GC-FID) |
|---|---|---|---|---|---|
| 12 | 0.20 | 0.52 | 1.14 | 0.48 | 4.6 |
| 13 | 0.15 | 0.66 | 1.41 | 0.24 | 6.1 |

The data in Table 6 shows a significant improvement in the thermal aging performance of Examples 7-13 compared to Example 5. The improved aging performance is attributed to compositions which contained hindered phenol or hindered phenol+phosphite additives added prior to the synthesis of 2. Increasing the amount of the hindered phenol+ phosphite additives (Examples 10-11) provided a further improvement in thermal stability (<1% mass loss after 10 days at less than 15% relative humidity).

Color Removal of Final Product Compositions

Example 18. A product composition similar to Example 7 (Control A) (748.22 g) and Ni 5249P (BASF product)

catalyst (7.51 g) was added to a 1 L Parr reactor vessel. The oxygen in the reactor was evacuated by purging with nitrogen gas until the oxygen level was under 1%. Hydrogen gas was then added to the reactor vessel to a pressure of 90-95 psi and the temperature was set to 140° C. The contents of the reactor were stirred continuously while the temperature of 140° C. and pressure of 95-105 psi was held for 4 hour. After 4 hours, the reaction mixture was allowed to cool to ambient temperature and the pressure was equilibrated to atmospheric. The contents of the flask were filtered to remove the Ni catalyst.

A sample was taken from the flask and analyzed for color (YI) and composition by GC-FID. The data is shown in Tables 7-8.

Example 19 A product composition similar to Example 7 (Control A) (83.38 g) and carbon black (8.34 g) were added to a 250 mL beaker and stirred for 1 hour at 40° C. After 1 hour the contents of the beaker were filtered to remove the carbon black.

A sample was taken from the flask and analyzed for color (YI) and composition by GC-FID. The data is shown in Tables 7-8.

Example 20. A product composition similar to Example 7 (Control A) (74.29 g) and basic alumina (7.43 g) were added to a 250 mL beaker and stirred for 1 hour at 40° C. After 1 hour the contents of the beaker were filtered to remove the alumina.

A sample was taken from the flask and analyzed for color (YI) and composition by GC-FID. The data is shown in Tables 7-8.

Example 21. A product composition similar to Example 5 (Control B) (92.77 g) and basic alumina (9.23 g) were added to a 250 mL beaker and stirred for 1 hour at 40° C. After 1 hour the contents of the beaker were filtered to remove the alumina.

A sample was taken from the flask and analyzed for color (YI) and composition by GC-FID. The data is shown in Tables 7-8.

Thermal Stability Mass Loss and UV Study of 2

Samples from Example 18 through 21 were then prepared and tested for mass loss in a forced air oven at 115° C. for 10 days. Stabilization additives were also added to some of the examples (18b, 19b, and 20b) as shown in Table 7. The additives and percent mass loss are shown in Table 7. The initial and final reaction compositions by GC-FID are shown in Table 8.

TABLE 7

Initial Color (YI) and Thermal Stability data for Examples 18-21

| Example | Wt % Irganox 1010 | Wt % Irgafos 168 | Mass Loss after 10 d (wt %) | Initial YI E313 [C/2] |
|---|---|---|---|---|
| Control A (No treatment) | 0 | 0 | 0.94 | 46 |
| 18a | 0 | 0 | 0.81 | 0 |
| 18b | 0.25 | 0.15 | 0.82 | 0 |
| 19a | 0 | 0 | 0.96 | 24 |
| 19b | 0.25 | 0.15 | 0.60 | 24 |
| 20a | 0 | 0 | 0.78 | 15 |
| 20b | 0.25 | 0.15 | 0.57 | 15 |
| Control B (No treatment) | 0 | 0 | 1.13 | 33 |
| 21 | 0 | 0 | 1.11 | 6 |

The data shows that the treatment methods of hydrogenation, basic alumina treatment, and carbon black significantly remove color from the original examples (Controls A-B). Hydrogenation with Ni catalyst (Example 18) removes all of the yellow color to produce a colorless product. Examples 18-20 show improved color (lower YI) and thermal stability (less % wt loss) over Control A. Example 21 showed an improvement in color (lower YI) and displayed approximately the same heat aging performance as Control B.

TABLE 8

Initial and Final composition for Examples 18-21 after Aging at 115° C. for 10 days at less than 15% relative humidity (RH).

| Example | 1 GC-FID Area % | 3 GC-FID Area % | 4 GC-FID Area % | 5 GC-FID Area % | 2 GC-FID Area % | 6 GC-FID Area % | Higher MW GC-FID Area % |
|---|---|---|---|---|---|---|---|
| Control A Initial | 0.17 | 0.15 | 0.23 | 0.58 | 98.13 | 0.33 | 0.24 |
| Control A after aging | 0.00 | 0.21 | 0.20 | 3.64 | 94.97 | 0.03 | 0.08 |
| 18a Initial | 0.23 | 0.70 | 0.20 | 0.14 | 97.16 | 0.03 | 0.33 |
| 18a after aging | 0.01 | 0.66 | 0.20 | 0.55 | 97.33 | 0.03 | 0.30 |
| 18b after aging | 0.00 | 0.64 | 0.06 | 0.24 | 97.64 | 0.03 | 0.60 |
| 19a Initial | 0.16 | 0.14 | 0.22 | 0.58 | 98.18 | 0.07 | 0.23 |
| 19a after aging | 0.00 | 0.21 | 0.20 | 3.42 | 95.14 | 0.05 | 0.07 |
| 19b after aging | 0.00 | 0.14 | 0.21 | 0.69 | 97.91 | 0.06 | 0.49 |
| 20 Initial | 0.17 | 0.25 | 0.21 | 0.57 | 98.10 | 0.07 | 0.23 |
| 20a after aging | 0.00 | 0.29 | 0.20 | 2.33 | 96.14 | 0.06 | 0.08 |
| 20b after aging | 0.00 | 0.22 | 0.20 | 0.65 | 97.77 | 0.06 | 0.52 |
| 21 Starting Material | 0.29 | 0.11 | 0.14 | 0.55 | 98.19 | 0.01 | 0.12 |
| 21 after aging | 0.00 | 0.19 | 0.14 | 4.02 | 94.70 | 0.03 | 0.07 |
| 21 Initial | 0.29 | 0.23 | 0.14 | 0.58 | 98.25 | 0.00 | 0.10 |
| 21 after aging | 0.00 | 0.24 | 0.14 | 3.09 | 95.57 | 0.03 | 0.09 |

The data in the table shows that the use of hindered phenol and phosphite additives aid in the stability of the overall composition regardless of the treatment method prior to aging at 115° C. In the absence of the additives, the composition has 4-7 times the quantity of 5 after aging at 115° C. for 10 days.

Example 18b and Example 10 were prepared and tested for mass loss and UV stability in a UV oven for 21 days. The UV oven had a UV lamp with a bulb output=0.10 J/cm$^2$ and 0.029 W/cm$^2$ max at 50-60° C. A UV-stabilizer additive (Tinuvin® 312, from BASF) was added to the Examples to produce Example 18c and Example 10b prior to aging. The additive amounts and percent mass loss are shown in Table 9. The initial and final reaction compositions by GC-FID are shown in Table 10.

TABLE 9

UV Thermal Stability data for product compositions

| Example | wt % Tinuvin 312 (BASF) | Day 21 % Mass Loss | 21 day YI E313 [C/2] | Initial YI E313 [C/2] |
|---|---|---|---|---|
| 18b | 0 | 8.00 | 3 | 0 |
| 18c | 0.2 | 2.14 | 1 | 0 |
| Example 10 | 0 | 10.95 | 28 | 17 |
| Example 10b | 0.2 | 1.17 | 18 | 17 |

The UV stabilizer preserves the weight loss degradation and the change of color of the products after exposure to UV light. Example 10b and 18c show a dramatic improvement in color (lower YI) and mass loss over Example 18b and Example 10 after aging for 21 day under UV exposure.

TABLE 10

Initial and Final composition after UV aging

| Example | 1 GC-FID Area % | 3 GC-FID Area % | 4 GC-FID Area % | 5 GC-FID Area % | 2 GC-FID Area % | 6 GC-FID Area % | Oligomers GC-FID Area % |
|---|---|---|---|---|---|---|---|
| 18b initial | 0.23 | 0.70 | 0.20 | 0.14 | 97.16 | 0.03 | 0.33 |
| 18b after UV aging | 0.05 | 7.67 | 0.22 | 14.58 | 63.69 | 0.47 | 3.22 |
| 18c after UV aging | 0.02 | 1.11 | 0.18 | 5.69 | 88.39 | 0.04 | 0.59 |
| Example 10 initial | 0.07 | 0.07 | 0.18 | 0.62 | 97.67 | 0.03 | 0.97 |
| Example 10 after UV aging | 0.03 | 3.74 | 0.11 | 30.07 | 45.16 | 0.35 | 2.36 |
| Example 10b after UV aging | 0.01 | 0.47 | 0.17 | 6.32 | 88.83 | 0.03 | 0.62 |

The data in the table shows that the use of a UV additive aids in the stability of the overall composition regardless of the treatment method (hydrogenation) prior to aging under UV light. In the absence of the UV additive, the composition has 2-5 times the quantity of 5 and 3-5 times the quantity of Oligomers after UV aging for 21 days.

For the following examples, this general procedure was used:

The composition comprising either Structure 2 or Structure 7 was formulated with additives as shown in Table 11. The additives and compositions were combined at room temp in a scintillation vial equipped with stir bar. The contents were then mixed at a 1400 rpm and heated to 120-150° C. until fully dissolved. Irganox® 1010 (I-1010), Irganox® 259 (I-259), Irganox® 245 (I-245), Irgafos® P-EPQ (PEPQ), Irganox® MD 1024 (MD 1024) are manufactured by BASF, Inc. Naugard 445 is manufactured by Chemtura, Inc. Phenothiazine (PTZ) is manufactured by Cytec Industries Inc.

TABLE 11

| Example | Description | Total % Mass Loss after 10 d at 110° C. |
|---|---|---|
| Comp Ex. 1 | 7 | 40.34 |
| Ex. 22 | 7 + 0.1% Ca Stearate | 6.45 |
| Ex. 23 | 7 + 0.25% I-1010 | 3.54 |
| Ex. 24 | 7 + 0.1% Zn Stearate | 6.12 |
| Ex. 25 | 7 + 0.1% Ca Stearate, 0.25% I-1010 | 2.66 |
| Ex. 26 | 7 + 0.1% Zn Stearate, 0.25% I-1010 | 3.6 |
| Ex. 27 | 7 + 0.1% Ca Stearate, 0.25% I-259 | 3.73 |
| Ex. 28 | 7 + 0.1% Ca Stearate, 0.25% I-245 | 2.22 |
| Ex. 29 | 7 + 0.1% Zn Stearate, 0.25% I-245 | 2.65 |
| Ex. 30 | 7 + 0.1% Ca Stearate, 0.25% PEPQ | 3.45 |
| Ex. 31 | 7 + 0.1% Ca Stearate, 0.25% MD1024 | 1.84 |
| Ex. 32 | 7 + 0.05% PTZ, 0.3% I-1010, 0.1% Naugard 445 | 3.22 |
| Comp. Ex. 2 | 2 | 18.83 |
| Ex. 33 | 2 + 0.1% Ca Stearate, 0.5% I-245 | 1.52 |
| Ex. 34 | 7 + 0.1% Ca Stearate, 0.5% I-245 | 2.45 |
| Ex. 35 | 7 + 0.1% Na Stearate, 0.5% I-245 | 1.77 |
| Ex. 36 | 7 + 0.1% Mg Stearate, 0.5% I-245 | 2.56 |

The data in Table 11 shows an improvement in the thermal performance of the compositions 2 and 7, by the addition of anti-oxidant and metal stearate additives. All of the Examples in Table 11 displayed lower evaporation rates of degradation products versus the Comparative Examples. It is surprising that by adding a small percentage of additive(s) has such a large effect on the ketal composition's thermal stability.

Test Description: IAU=Index of absorption units, calculated by integrating the area under the UV spectrum from 380 nm to 500 nm using a UV-VIS detector. This is a quantitative measurement for the presence of visual color. Samples are usually dissolved in methanol before measurement, up to 50 wt %. A background scan of methanol is performed before the sample is analyzed.

Hydrogenation of 7

The procedure for Examples 37 through 39 was similar to Example 18, except that the catalyst type, temperature, time, and hydrogen pressure were according to Table 12.

TABLE 12

Hydrogenation Initial and Final Reaction compositions

| Example | Hydrogenated Material | Catalyst | Temp. (° C.) | Pressure (psi) | Time (hrs) | IAU Index |
|---|---|---|---|---|---|---|
| 37 initial | 7 | 0.1% | 140 | 520 | 4 | 0.225 |
| 37 final |  | Ni249P |  |  |  | 0.148 |
| 38 initial | 7 | 0.1% | 70 | 100 | 4 | 0.711 |
| 38 final |  | Ni249P |  |  |  | 0.266 |
| 39 initial | 7 | 0.1% | 140 | 500 | 4 | 0.255 |
| 39 final |  | Ni249P |  |  |  | 0.148 |

Example 40. 2 (748.22 g) and Ni 5249P catalyst (7.51 g) was added to the 1 L Parr reactor vessel. The oxygen in the reactor was evacuated by purging with nitrogen gas until the oxygen level was under 1%. Hydrogen gas was then added to the reactor vessel to a pressure of 90-95 psi and the temperature was set to 140° C. The contents of the reactor were stirred continuously while the temperature of 140° C. and pressure of 95-105 psi was held for 4 hour. After 4 hour, the reaction mixture was allowed to cool to ambient temperature and the pressure was equilibrated to atmospheric. The contents of the flask were filtered to remove the Ni catalyst.

A sample was taken from the flask and analyzed for the YI number and by GC-FID. The composition by GC-FID and YI are shown in Table 13.

TABLE 13

Initial and Final composition for Example 40

| Example | YI E313 [C/2] | 2 Area % (GC-FID) |
|---|---|---|
| 40 initial | 46.49 | 98.1 |
| 40 final | 0 | 97.2 |

Although the present invention has been described with reference to preferred embodiments, persons skilled in the art will recognize that changes may be made in form and detail without departing from the spirit and scope of the invention. All references cited throughout the specification, including those in the background, are incorporated herein in their entirety. Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A process to prepare a plasticizer, wherein the plasticizer has a molecular weight of greater than 300 with at least 2 alkyl ketal ester moieties, comprising the step:

contacting under reaction conditions, an alkyl ketal ester, a multihydric hydrocarbyl moiety, or a monohydric alkyl ketal ester; a catalyst; an antioxidant; and optionally a thermal stabilizer or mixtures thereof.

2. The process of claim 1, wherein the plasticizer has a formula comprising:

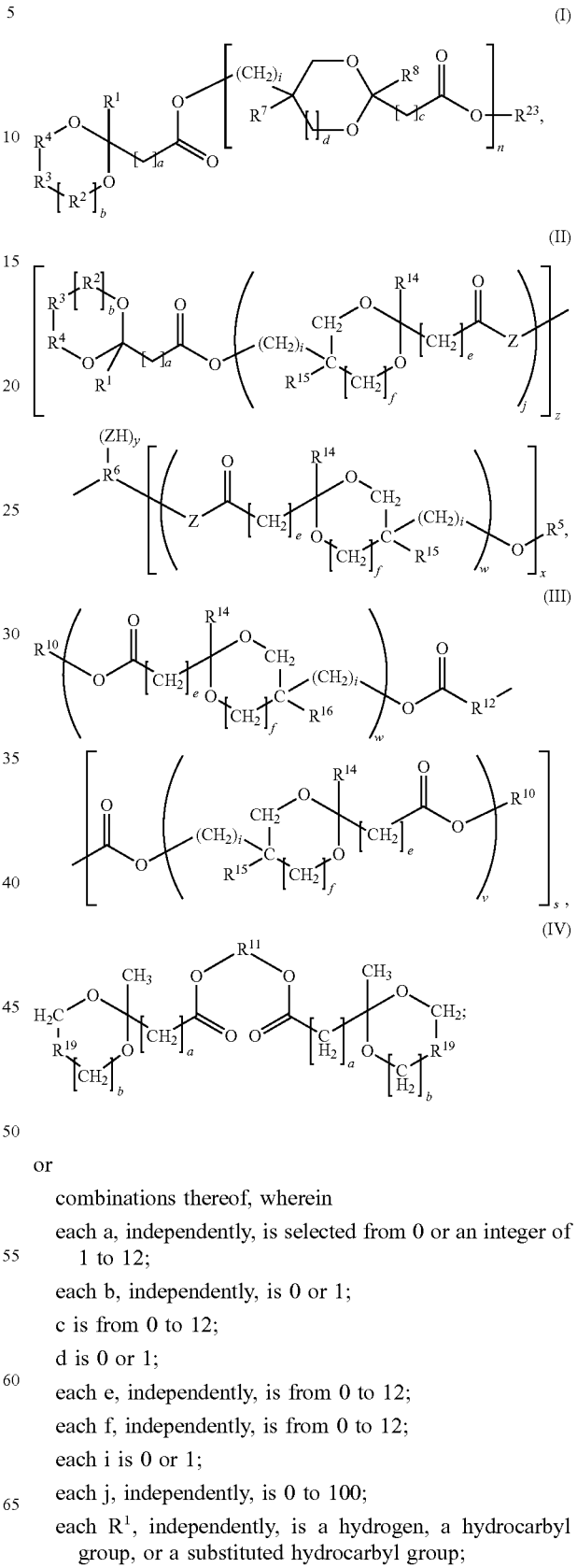

or combinations thereof, wherein each a, independently, is selected from 0 or an integer of 1 to 12;

each b, independently, is 0 or 1;

c is from 0 to 12;

d is 0 or 1;

each e, independently, is from 0 to 12;

each f, independently, is from 0 to 12;

each i is 0 or 1;

each j, independently, is 0 to 100;

each $R^1$, independently, is a hydrogen, a hydrocarbyl group, or a substituted hydrocarbyl group;

each $R^2$, $R^3$ and $R^4$ are independently methylene, alkylmethylene, or dialkylmethylene;

$R^5$ is a hydrogen or

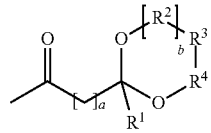

$R^6$ is a hydrocarbyl group or a substituted hydrocarbyl group;

each $R^7$, independently, is a hydrogen, a hydrocarbyl or a substituted hydrocarbyl group;

each $R^8$, independently, is a hydrogen, a hydrocarbyl or a substituted hydrocarbyl group;

each $R^{10}$, independently, is a hydrocarbyl or a substituted hydrocarbyl group;

$R^{11}$ is a hydrocarbyl group, or a substituted hydrocarbyl group;

$R^{12}$, is a covalent bond, a hydrocarbyl group or a substituted hydrocarbyl group;

each $R^{14}$, independently, is a hydrogen, a hydrocarbyl, or a substituted hydrocarbyl group;

each $R^{15}$, independently, is a hydrogen, a hydrocarbyl, or a substituted hydrocarbyl group;

each $R^{19}$, independently, is a hydrocarbyl group, a substituted hydrocarbyl group, or a hydrocarbyl group substituted with up to 5 hydroxyl groups;

each $R^{23}$ is a hydrocarbyl group or substituted hydrocarbyl group having between 1 and 12 carbon atoms each Z, independently, is —O—, —NH— or —NR— where R is a hydrocarbyl or a substituted hydrocarbyl group;

n is from 1 to 100;
s is at least one;
v is from 0 to 100;
w is from 1 to 100;
x is at least 1;
y is 0 or a positive number.

3. The process of claim 2, wherein the plasticizer is the compound of formula (IV) wherein $R^{11}$ is a C4 alkyl.

4. The process of claim 3, wherein each a=2 and each b=0.

* * * * *